(12) United States Patent
Gomi et al.

(10) Patent No.: US 7,883,613 B2
(45) Date of Patent: Feb. 8, 2011

(54) CAPILLARY ELECTROPHORESIS APPARATUS

(75) Inventors: Takashi Gomi, Hitachinaka (JP); Ryoji Inaba, Hitachinaka (JP); Motohiro Yamazaki, Mito (JP); Hidenori Namba, Naka (JP); Jin Matsumura, Hitachinaka (JP); Hiromi Yamashita, Ishioka (JP); Seiichi Ugai, Hitachinaka (JP); Kazumichi Imai, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 534 days.

(21) Appl. No.: 11/806,889

(22) Filed: Jun. 5, 2007

(65) Prior Publication Data

US 2007/0278101 A1 Dec. 6, 2007

(30) Foreign Application Priority Data

Jun. 5, 2006 (JP) .............................. 2006-156052

(51) Int. Cl.
*G01N 27/453* (2006.01)
(52) U.S. Cl. ........................ 204/601; 204/602; 204/603; 204/604
(58) Field of Classification Search ......... 204/450–470, 204/600–621
See application file for complete search history.

(56) References Cited

U.S. PATENT DOCUMENTS

| | | | |
|---|---|---|---|
| 4,985,129 A | 1/1991 | Burd | |
| 6,383,356 B1* | 5/2002 | Hayashizaki et al. | 204/605 |
| 6,936,152 B2* | 8/2005 | Kojima et al. | 204/601 |
| 7,361,259 B2* | 4/2008 | Goudberg et al. | 204/603 |
| 2003/0102221 A1* | 6/2003 | Ozawa et al. | 204/601 |
| 2003/0201180 A1* | 10/2003 | Furukawa et al. | 204/452 |
| 2004/0231438 A1* | 11/2004 | Schwartz | 73/864.17 |
| 2006/0006066 A1* | 1/2006 | Yamazaki et al. | 204/451 |

FOREIGN PATENT DOCUMENTS

| | | |
|---|---|---|
| JP | 2-245654 | 10/1990 |
| JP | 2003-346828 | 12/2000 |
| JP | 2002-039992 | 2/2002 |
| JP | 2003-166976 | 6/2003 |
| JP | 2005-077293 | 3/2005 |
| JP | 2006-119158 | 5/2006 |

OTHER PUBLICATIONS

Japanese Office Action issued in Japanese Patent Application No. JP 2006-156052, dated Aug. 26, 2008.

* cited by examiner

*Primary Examiner*—Alexa D Neckel
*Assistant Examiner*—Jennifer Dieterle
(74) *Attorney, Agent, or Firm*—McDermott Will & Emery LLP

(57) ABSTRACT

The present invention provides a capillary electrophoresis apparatus in which a capillary is easily attached to and detached from a migration medium filling unit without mixing impurities into the capillary. Mixture of impurities such as dust is also prevented when a capillary negative-electrode end is brought into contact with a sample stored in a vessel. Furthermore, temperature control is efficiently performed in the capillary. In the capillary electrophoresis apparatus, the whole of capillary array can be supported by grasping a grip portion by hand. A migration medium filling mechanism includes a slide mechanism which moves a polymer block with respect to a capillary head. The capillary electrophoresis apparatus includes a vessel in which a sample and a buffer can simultaneously be stored. Temperatures of the capillary and an irradiation and detection unit are controlled by a temperature control function provided in a thermostatic device.

17 Claims, 15 Drawing Sheets

CAPILLARY ELECTROPHORESIS APPARATUS

BACKGROUND OF THE INVENTION

1. Field of the Invention

The present invention relates to a capillary electrophoresis apparatus which separates and analyzes a nucleic acid and a protein.

2. Description of the Related Art

Recently a capillary electrophoresis apparatus has been developed to separate and analyze a nucleic acid and a protein. The capillary electrophoresis apparatus includes a capillary, a power supply which applies high voltage at the both ends of the capillary, an irradiation system which irradiates the capillary with a laser beam, a light acceptance optical detection unit which detects fluorescence from a region irradiated with the laser beam, a thermostatic device which controls a capillary temperature, and a migration medium filling unit which fills the capillary with a migration medium.

The capillary is attached to and detached from the migration medium filling unit during capillary exchange. At this point, because the capillary or a capillary head is grasped by hand or a tool, impurities are possibly mixed into the migration medium through the hand or tool. The migration medium also possibly adheres to an operator. It is necessary to move the capillary by a length in which the capillary or capillary head is inserted into the migration medium filling unit. In such cases, the capillary is possibly broken due to carelessness of the operator. Therefore, it is not easy to attach and detach the capillary to and from the migration medium filling unit.

In order to enhance detection accuracy of the capillary electrophoresis apparatus, it is necessary that the capillary is kept at a constant temperature. Conventionally, a temperature control system of the capillary electrophoresis apparatus separately has a temperature control mechanism which controls a temperature of a capillary detection unit and a thermostatic bath which controls a temperature of a region ranging from the capillary detection unit to a capillary negative-electrode end. That is, the temperature of the capillary is controlled by the plural temperature controller in the conventional capillary electrophoresis apparatus.

[Patent Document 1] Japanese Patent Application Laid-Open No. 2002-039992

[Patent Document 2] Japanese Patent Application Laid-Open No. 2003-166976

SUMMARY OF THE INVENTION

In view of the foregoing, an object of the invention is to provide a capillary electrophoresis apparatus in which no impurity is mixed into the capillary while the capillary is easily attached to and detached from the migration medium filling unit.

Another object of the invention is to provide a capillary electrophoresis apparatus in which mixture of the impurities such as dust can be prevented when the capillary negative-electrode end is brought into contact with a sample stored in a vessel.

Still another object of the invention is to provide a capillary electrophoresis apparatus which can efficiently control the temperature of the capillary.

The invention relates to a capillary electrophoresis apparatus configured to house a capillary array in a thermostatic device.

In a capillary electrophoresis apparatus of the invention, the whole of a capillary array can be supported by grasping a grip portion by hand. A migration medium filling mechanism has a slide mechanism which moves a polymer block with respect to a capillary head.

A capillary electrophoresis apparatus of the invention has a vessel in which a sample and a buffer can simultaneously be stored.

In a capillary electrophoresis apparatus of the invention, a temperature control function provided in a thermostatic device provides the temperature control for the capillary and the optical detection unit.

According to the invention, the capillary is easily attached to and detached from the migration medium filling unit, and the mixture of the impurities into the capillary can be prevented.

Furthermore, according to the invention, the mixture of the impurities such as dust can be prevented when the capillary negative-electrode end is brought into contact with the sample stored in the vessel.

Furthermore, according to the invention, the temperature of the capillary can efficiently be controlled.

DESCRIPTION OF THE PREFERRED EMBODIMENTS

A novel characteristic and benefit of the invention will be described below with reference to the drawings. However, the drawings are illustrated only by way of example, and the invention is not limited to the drawings. Examples can appropriately be combined.

Figure 1:
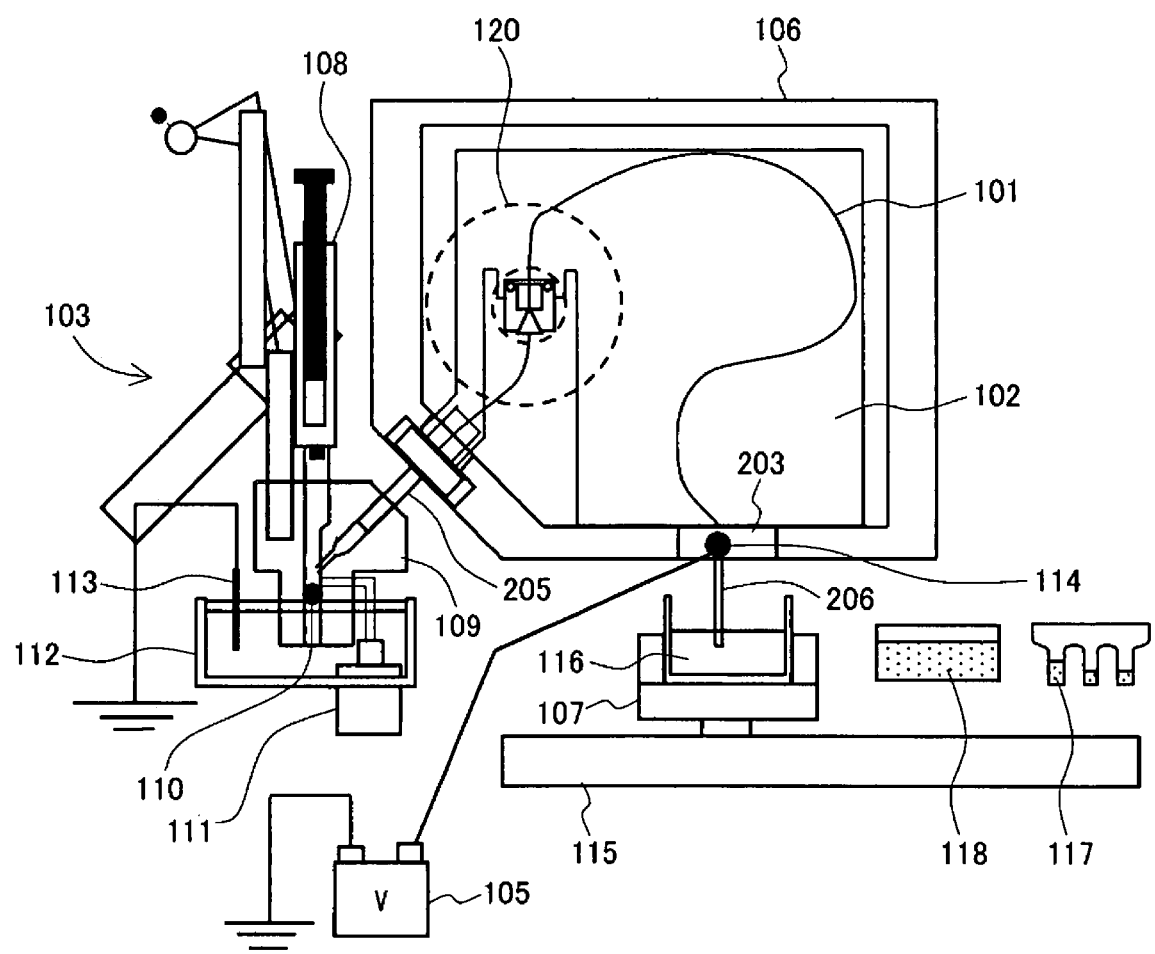
FIG. 1 shows schematic configuration of a capillary electrophoresis apparatus according to an exemplary embodiment of the invention.

FIG. 1 shows an outline of a capillary electrophoresis apparatus according to an exemplary embodiment of the invention. The capillary electrophoresis apparatus of this embodiment includes a capillary array 102, a polymer filling unit 103, an irradiation and detection unit 120, a high-voltage power supply 105, a thermostatic device 106, and a conveyer 115. The capillary array 102 includes single or plural capillaries 101. The polymer filling unit 103 injects a polymer into the capillary 101. The irradiation and detection unit 120 irradiates a sample in the capillary 101 with light to detect fluorescence of the sample. The high-voltage power supply 105 applies high voltage to the capillary 101. The thermostatic device 106 keeps the capillary 101 at a constant temperature. The conveyer 115 includes a movable stage 107.

The capillary 101 is an exchangeable member, and the capillaries 101 are exchanged when a measuring method is changed or when the breakage or degradation is generated in the capillary 101. The capillary 101 is formed of a glass tube which has tens to hundreds micrometer inner diameter and has hundreds micrometer outer diameter. A surface of the capillary 101 is coated with polyimide. An inside of the capillary 101 is filled with a separation medium to impart a migration speed difference during the electrophoresis. The separation medium includes a fluid separation medium and non-fluid separation medium. In the embodiment, a fluid polymer is used.

A capillary head 205 is provided at one end of the capillary 101, and a capillary negative-electrode end 206 is formed at the other end. The capillary head 205 is formed by bundling end portions of the capillaries 101, and the capillary head 205 has a function of connecting the polymer filling unit 103 and the capillary 101. The capillary negative-electrode end 206 gets in contact with the sample, a solution and the like. The capillary 101 is fixed by a load header 203 on the capillary negative-electrode end side. A negative electrode 114 is provided in the load header 203.

The irradiation and detection unit 120 includes an irradiation system and a detection system. The irradiation system has a function of irradiating a portion where polyimide coating film is removed in the capillary 101, i.e., a detection portion with excitation light. The detection system has a function of detecting the fluorescence from the sample in the detection portion of the capillary 101. The sample is analyzed from the light detected by the detection system.

The polymer filling unit 103 includes a syringe 108, a polymer block 109, a check valve 110, a polymer vessel 111, and a positive-electrode buffer vessel 112. The capillary 101 is connected to a flow path in the polymer block 109 by connecting the capillary head 205 to the polymer block 109. The capillary 101 is filled or refilled with polymer in the polymer vessel 111 through the flow path in the polymer block 109 by an operation of the syringe 108. The capillary 101 is refilled with the polymer in each measurement in order to improve measuring performance.

A positive electrode 113 is arranged in the positive-electrode buffer vessel 112. The high-voltage power supply 105 applies the high voltage of about 15 kV between the positive electrode 113 and the negative electrode 114.

In the thermostatic device 106, the capillary array 102 is sandwiched in a planar manner to keep the capillaries 101 at a constant temperature by a heat insulation material and a temperature control member to which a heater is attached. A temperature sensor is attached to the temperature control member to perform feedback control. The capillary head 205 and the load header 203 are fixed to the thermostatic device 106, which allows the capillary array 102 to be fixed at a desired position.

The conveyer 115 includes three electric motors and linear guides to move the movable stage 107, and the conveyer 115 can move the movable stage 107 in three axis directions of a vertical direction, a horizontal direction, and a depth direction. The movable stage 107 can conveys a buffer vessel 116, a washing vessel 118, a waste water vessel, and a sample plate 117 to the capillary negative-electrode end 206 if needed.

Figure 2:
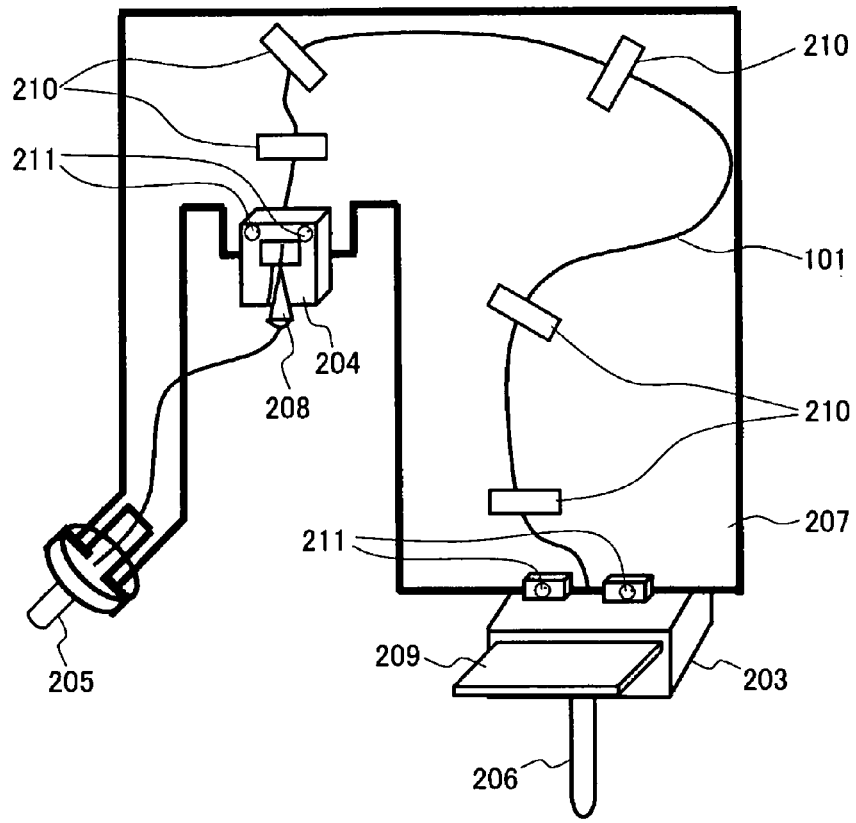
FIG. 2 shows details of a capillary array and a capillary head of the capillary electrophoresis apparatus of the embodiment.
Figure 2:
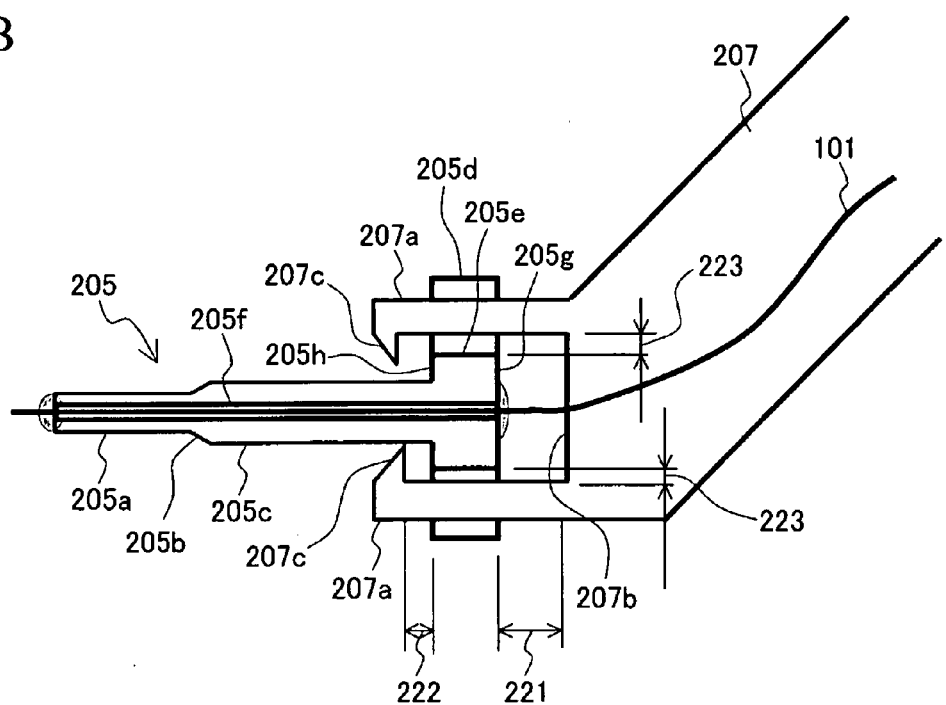

FIG. 2A shows a detail of the capillary array 102 in the capillary electrophoresis apparatus of FIG. 1. The capillary head 205 is provided at one end of the capillary 101, and the capillary negative-electrode end 206 is formed at the other end. A metal hollow electrode is attached to the load header 203. The capillary negative-electrode end 206 pierces through the hollow electrode, and the capillary negative-electrode end 206 is projected from the end of the hollow electrode. The capillary 101 is fixed onto an array sheet 207 with tapes 210. The array-sheet 207 is fixed to the load header 203 with resin rivets 211. A grip portion 209 provided in the load header 203 will be described later.

A first example of the irradiation and detection unit 120 will be described. The irradiation and detection unit 120 of the first example includes a conical lens 208 and a reference base 204. The reference base 204 is fixed to the array sheet 207 with the resin rivets 211. The detection portion of the capillary 101 is held on the reference base 204. The detection portion of the capillary 101 is irradiated with the excitation light emitted from the light source through the conical lens 208.

A second example of the irradiation and detection unit 120 will be described. In the second example, it is assumed that the capillary array 102 includes the plural capillaries 101. The capillaries 101 are arrayed in parallel with one another on the reference base 204. A laser light source such as argon ion laser is used in the irradiation system. The laser beam from the light source is split into two laser beams by a beam splitter and a mirror. The two laser beams are collected by collective lenses respectively, and the capillary 101 are irradiated with the laser beams.

The two laser beams are irradiated from both lateral sides of the capillary array, i.e., from directions orthogonal to the capillary 101. Only one lateral side of the capillary array may be irradiated with the laser beam without dividing the laser beam.

The capillary 101 is irradiated with the laser beam such that the laser beam becomes parallel to a plane formed by the array of the capillaries 101. That is, capillary 101 is irradiated with the laser beam such that the laser beam becomes parallel to a plane of the reference base 204 holding the capillaries 101.

When the capillary 101 is filled with the migration medium, the laser beam propagates sequentially through the capillaries 101 to pierce through from one lateral side of the array of the capillaries 101 to the other lateral side. Accordingly, all the capillaries 101 are efficiently irradiated at the same time.

A spread beam method may be adopted in the irradiation system. In the spread beam method, the laser beam from the light source is spread by a beam expander, and the laser beam is caused to converge in a line shape by the cylindrical lens.

Then, the capillaries 101 are irradiated with the laser beam from the direction perpendicular to the plane formed by the array of the capillaries 101. In the spread beam method, because all the capillaries 101 are simultaneously irradiated with the laser beam, the capillaries 101 can be irradiated with the laser beam having the substantially same laser intensity irrespective of an arrangement variation of the capillaries 101.

FIG. 2B is an enlarged view of the capillary head 205. The capillary head 205 includes a front end 205a, a conical portion 205b, a cylindrical portion 205c, and a collar portion 205d. These components are concentrically arranged. Their outer diameters are increased in the order of the front end 205a, the cylindrical portion 205c, and the collar portion 205d. The front end 205a and the cylindrical portion 205c have circular cross section. The collar portion 205d is formed in a disc shape having notches 205e on both sides in a diameter direction. A hole 205f is formed along a central axis line in the capillary head 205, and the capillary 101 is arranged in the hole 205f. The capillary 101 and the capillary head 205 are fixed to each other with a bonding agent. The capillary 101 is slightly projected from the front end 205a.

The array sheet 207 has a U-shape portion at a front end thereof. The U-shape portion includes a bottom 207b and two projections 207a which are parallel to each other. Pawls 207c are formed at front ends of the projections 207a so as to face each other. The two projections 207a are engaged with notches 205e of the collar portion 205d of the capillary head 205.

A gap 221 is formed between an end face 205g of the collar portion 205d of the capillary head 205 and a bottom 207b in the U-shape portion at the front end of the array sheet 207. A gap 222 is formed between the pawls 207c of the projections 207a and a circumferential surface 205h of the collar portion 205d. Gaps 223 are provided between the two projections 207a and the notches 205e of the collar portion 205d of the capillary head 205.

The capillary head 205 can be moved along the axis line direction relative to the array sheet 207 by providing the gaps 221 and 222 in the axis line direction. The end face 205g of the collar portion 205d of the capillary head 205 abuts on the bottom 207b in the U-shape portion at the front end of the array sheet 207, which prevents the capillary head 205 from being further moved with respect to the array sheet 207. The circumferential surface 205h of the collar portion 205d of the capillary head 205 abuts on the pawl 207c of the projection 207a of the array sheet 207, which prevents the capillary head 205 from being further moved toward the direction in which the capillary head 205 is separated away from the array sheet 207.

The capillary head 205 can be moved along a radial direction relative to the array sheet 207 by providing the gaps 223 in the radial direction. The notch 205e of the collar portion 205d of the capillary head 205 abuts on the projection 207a of the array sheet 207, which prevents the capillary head 205 from being further moved in the radial direction.

Figure 3:
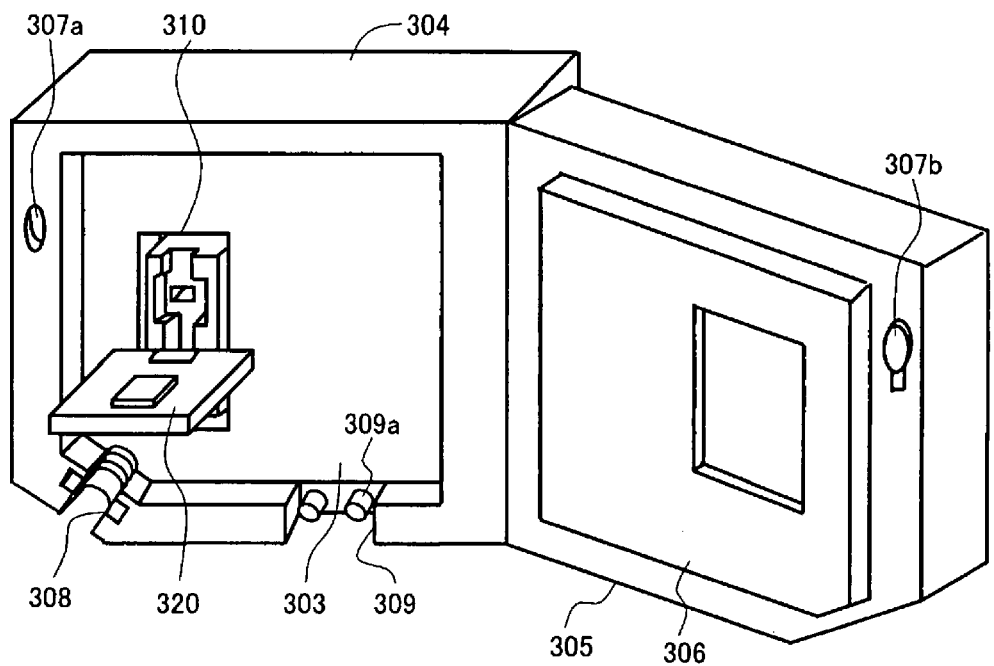
FIG. 3 shows a method of attaching the capillary array to a thermostatic device of the capillary electrophoresis apparatus of the embodiment.
Figure 3:
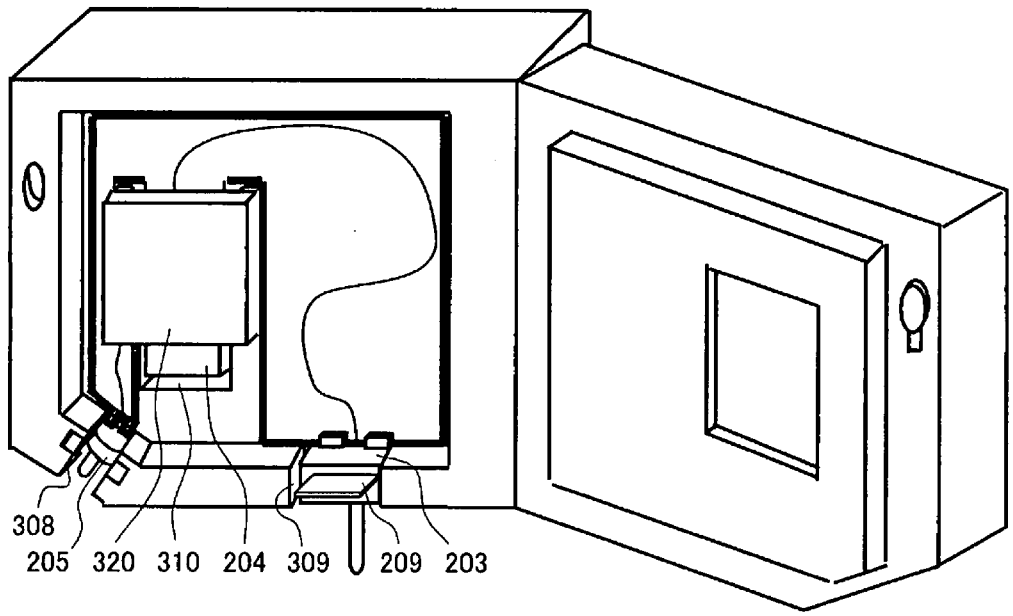

A structure of the thermostatic device 106 and a method of attaching the capillary array 102 to the thermostatic device 106 will be described with reference to FIG. 3. As shown in FIG. 3A, the thermostatic device 106 includes a main body frame 304 and a door frame 305. A temperature control member 303 is placed in the main body frame 304. An optical detection unit holder 310 and an optical detection unit holder cover 320 are arranged in the main body frame 304. The optical detection unit holder 310 is formed with high accuracy, and the optical detection unit holder 310 is covered with the optical detection unit holder cover 320. A notch portion 309 is formed in the main body frame 304, and projections 309a are provided in the notch portion 309. Grooves 308 are formed in the main body frame 304.

A capillary array pressing sponge 306 is attached to the door frame 305. When the door frame 305 is closed, a lock 307a of the main body frame 304 is engaged with a lock 307b of the door frame 305.

Then, a method of attaching the capillary array 102 to the thermostatic device 106 will be described. The whole of the capillary array 102 can be held by holding a grip portion 209 of the load header 203 with one hand. The capillary array 102 is inserted into the main body frame 304 while the grip portion 209 of the load header 203 is held with one hand. At this point, as shown in FIG. 3B, the capillary array 102 is arranged such that the reference base 204 of the irradiation and detection unit 120 is engaged with a reference base groove of the optical detection unit holder 310, such that the load header 203 is engaged with the notch portion 309, and such that the capillary head 205 is engaged with the grooves 308.

Then, the optical detection unit holder cover 320 is attached to the optical detection unit holder 310. Finally, the door frame 305 is closed to seal the thermostatic device 106.

The capillary 101 is always kept at a constant temperature because the capillary 101 is sandwiched between the temperature control member 303 of the main body frame 304 and the capillary array pressing sponge 306 of the door frame 305. The temperature control function will be described later.

Figure 4:
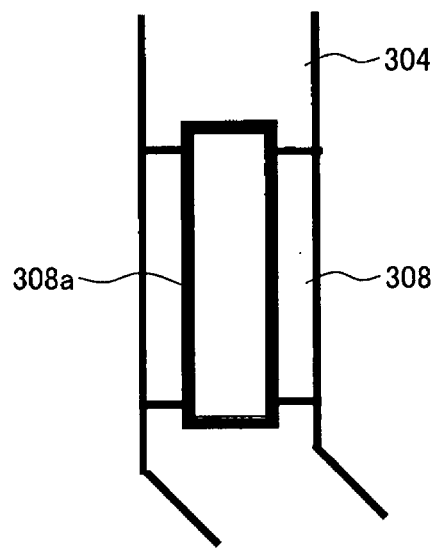
FIG. 4 shows details of an attachment portion of the capillary head and a thermostatic device frame of the capillary electrophoresis apparatus of the embodiment.
Figure 4:
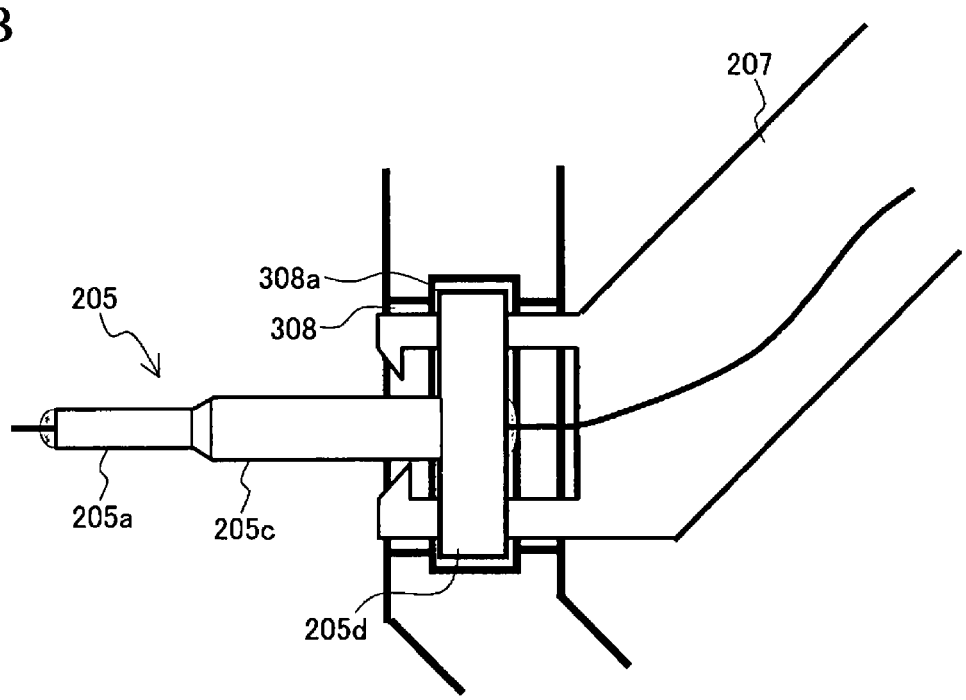

A method of attaching the capillary head 205 into the grooves 308 of the main body frame 304 of the thermostatic device 106 will be described with reference to FIG. 4. As shown in FIG. 4A, an arc groove 308a having an arc bottom surface is further formed in a bottom surface of the groove 308 of the main body frame 304. As shown in FIG. 4B, the capillary head 205 is attached to the main body frame 304 such that the collar portion 205d of the capillary head 205 is engaged with the arc groove 308a. A diameter of the arc groove 308a is larger than an outer diameter of the collar portion 205d of the capillary head 205 by about 1.5 mm. A width of the arc groove 308a is larger than a thickness of the collar portion 205d of the capillary head 205 by about 1.5 mm. The capillary head 205 can be moved in such a range that the collar portion 205d can be moved within the arc groove 308a.

As described above, the capillary head 205 can be moved along the axis line direction and the radial direction relative to the array sheet 207. Accordingly, when the array sheet 207 is arranged at an optimum position in the main body frame 304, because the collar portion 205d of the capillary head 205 is automatically moved along an edge of the arc groove 308a of the main body frame 304, the capillary head 205 is arranged in the groove 308 of the main body frame 304.

A structure of the polymer filling unit 103 of the capillary electrophoresis apparatus according to the embodiment of the invention will be described below with reference to FIG. 5. The polymer filling unit 103 includes the syringe 108, the polymer block 109, the check valve 110, the polymer vessel 111, the positive-electrode buffer vessel 112, and the slide mechanism 601. A positive electrode 113 is arranged in the positive-electrode buffer vessel 112. A hole 109a into which the capillary head 205 is inserted is formed in the polymer block 109. The hole 109a has a shape corresponding to the front end 205a and conical portion 205b of the capillary head 205, and the inner diameter of the hole 109a is slightly larger than the outer diameter of the front end 205a of the capillary head 205. A chamfering portion is formed at an entrance of the hole 109a, and the chamfering portion has an angle slightly larger than that of the conical portion 205b of the capillary head 205.

The slide mechanism 601 includes two slide guides 602, a first stage 603a, a second stage 603b, a spring 604, a block support member 605, a first rod 607, a second rod 608, a triangular member 609, and a lever 610. The slide guides 602 are formed by two cylindrical rods parallel to each other. The slide guides 602 are fixed to a chassis of the capillary electrophoresis apparatus.

Two holes are formed in the first and second stages 603a and 603b respectively, the holes have the substantially same inner diameter as the outer diameter of the slide guide 602. The slide guides 602 pierce through the holes of the first and second stages 603a and 603b, and the first and second stages 603a and 603b can be moved along the slide guides 602. The first and second stages 603a and 603b are coupled to each other by the spring 604.

The slide guides 602 form moving paths of the first and second stages 603a and 603b. The moving paths formed by the slide guides 602 are parallel to the axis line of the hole 109a formed in the polymer block 109. The capillary head 205 is inserted into the hole 109a. That is, the hole 109a of the polymer block 109 and the slide guide 602 are arranged in parallel with each other.

Because the first stage 603a is coupled to the polymer block 109 through the block support member 605, the first stage 603a, the block support member 605, and the polymer block 109 are integrally moved. That is, the first stage 603a, the block support member 605, and the polymer block 109 are moved in parallel with the slide guide 602. The syringe 108, the check valve 110, the polymer vessel 111, and the positive electrode buffer vessel 112 are connected to the polymer block 109. These members and components are moved in parallel with the slide guide 602, along with the polymer block 109.

A rectangular groove 612 is formed at one end of the first rod 607, and a projection 613 is provided at the other end. The first rod 607 is rotatably attached to the chassis of the capillary electrophoresis apparatus by a pin 621. That is, the first rod 607 is able to pivot about the pin 621.

The second rod 608 includes a first portion 608a and a second portion 608b, and the first portion 608a and the second portion 608b are coupled to each other with a spring 611. Accordingly, the second portion 608b of the second rod 608 can coaxially be moved with respect to the first portion 608a. The first portion 608a of the second rod 608 is rotatably attached to the second stage 603b by a pin 622. That is, the second rod 608 is able to pivot about the pin 622 on the second stage 603b.

A first end of the triangular member 609 is attached to the lever 610. The lever 610 is rotatably attached to the chassis of the capillary electrophoresis apparatus. A second end of the triangular member 609 is rotatably attached to the second portion 608b of the second rod 608 by a pin 623. A pin 624 is provided at a third end of the triangular member 609, and the pin 624 is engaged with the rectangular groove 612 of the first rod 607.

The lever 610 is rotated counterclockwise to insert the capillary head 205 into the hole 109a of the polymer block 109 using the slide mechanism 601. When the lever 610 is rotated counterclockwise, the triangular member 609 and the lever 610 are rotated about the central axis line of the lever 610. When the triangular member 609 is rotated, the first rod 607 pivots about the pin 621, and the second rod 608 pivots about the pin 622. When the lever 610 is turned one round counterclockwise, the first rod 607 and the second rod 608 perform one-time reciprocal movement.

When the first rod 607 pivots about the pin 621, the projection 613 abuts on the second stage 603b to push up the second stage 603b. The first rod 607 forms a lever in which the pin 624 is a power point, the pin 621 is a fulcrum, and the front end of the projection 613 is a point of action. The projection 613 can obtain large force by the principle of leverage. Even if the triangular member 609 applies the small force to the pin 624 at the third end, the large force acts on the front end of the projection 613 by the principle of leverage. Accordingly, even if a small torque acts on the lever 610, the large force acts on the front end of the projection 613.

The second stage 603b is moved obliquely upward along the slide guide 602. Because the second stage 603b and the first stage 603a are connected by the spring 604, the first stage 603a is also moved along the slide guide 602. When the first stage 603a is moved, the polymer block 109 is moved in parallel with the slide guide 602. The syringe 108, the check valve 110, the polymer vessel 111, and the positive electrode buffer vessel 112 are moved along with the polymer block 109.

On the other hand, the capillary head 205 attached to the thermostatic device 106 is held at a predetermined position. When the polymer block 109 is moved, the capillary head 205 is engaged with the hole 109a of the polymer block 109.

Figure 6A:
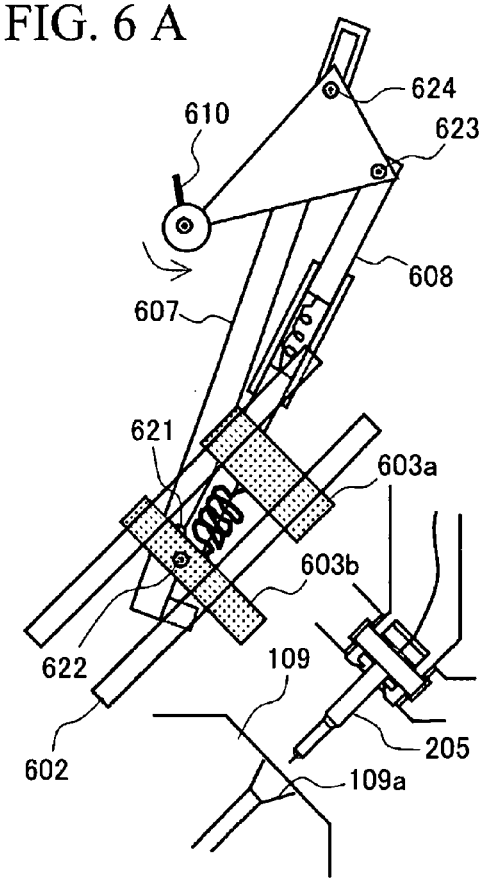
FIG. 6 shows an operation of a slide mechanism in the first example of a polymer filling unit of the capillary electrophoresis apparatus of the embodiment.

The operation of the polymer filling unit 103, particularly the operation of the slide mechanism 601 of the capillary electrophoresis apparatus according to the embodiment of the invention will be described below with reference to FIG. 6. Only the slide mechanism 601, the capillary head 205, and the hole 109a formed in the polymer block 109 are shown in FIG. 6. As shown in FIG. 6A, an operator manually rotates the lever 610 counterclockwise. When the lever 610 is rotated counterclockwise, the triangular member 609 attached to the lever 610 is rotated about the central axis line of the lever 610. The pin 623 at the second end and the pin 624 at the third end of the triangular member 609 are also moved so as to draw an arc about the central axis line of the lever 610.

The pin 624 at the third end of the triangular member 609 draws the arc while engaged with the rectangular groove 612 of the first rod 607. This enables the first rod 607 to pivot about the pin 621. The pin 623 at the second end of the triangular member 609 draws the arc while attached to the second portion of the second rod 608. This enables the second rod 608 to pivot about the pin 622 on the second stage 603b. At this point, the second portion 608b is moved along the axis line direction relative to the first portion 608a, which absorbs a change in distance between the pin 623 at the second end of the triangular member 609 and the pin 622 on the second stage 603b.

When the pin 623 at the second end and the pin 624 at the third end of the triangular member 609 are located on the lower side, the first and second stages 603a and 603b are arranged on the lower sides of the two slide guides 602. At this point, the polymer block 109 is located away from the capillary head 205. When the lever 610 is rotated counterclockwise, the pin 623 at the second end and the pin 624 at the third end of the triangular member 609 are moved upward, and the first and second stages 603a and 603b are moved obliquely upward on the two slide guides 602. The polymer block 109 is located at the position in which the polymer block 109 is brought close to the capillary head 205.

Figure 6B:
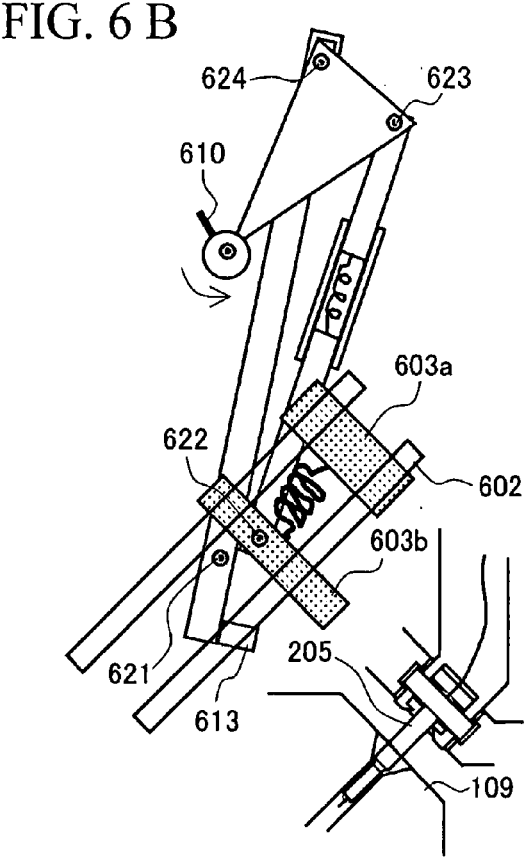

As shown in FIG. 6B, when the lever 610 is further rotated counterclockwise, the pin 623 at the second end and the pin 624 at the third end of the triangular member 609 are further moved upward. The polymer block 109 is brought further close to the capillary head 205.

Figure 6C:
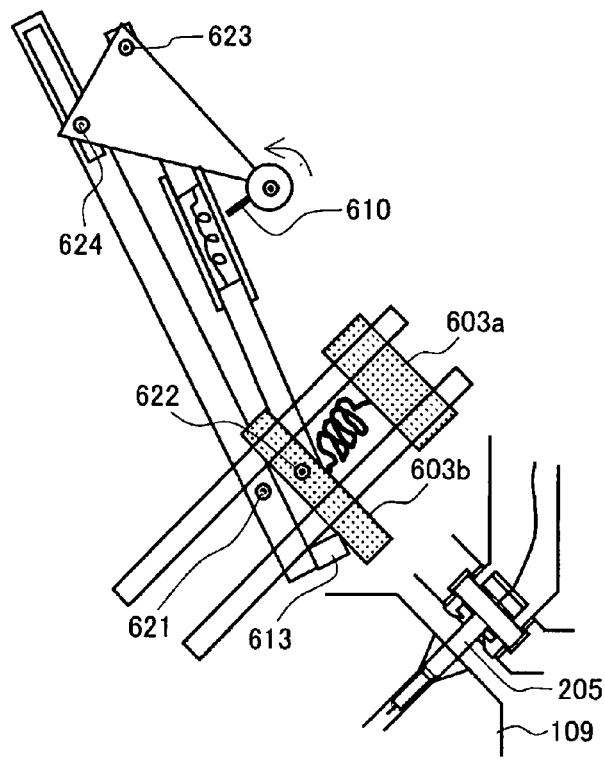

As shown in FIG. 6C, when the lever 610 is further rotated counterclockwise, the pin 623 at the second end and the pin 624 at the third end of the triangular member 609 are moved downward. The polymer block 109 is brought further close to the capillary head 205. At this point, the projection 613 at the lower end of the first rod 607 abuts on the second stage 603b. When the lever 610 is further rotated counterclockwise, the first rod 607 further pivots, and the second stage 603b is pushed up through the projection 613. As described above, even if the small force acts on the pin at the third end of the triangular member 609, the large force acts on the projection 613 by the principle of leverage.

When the second stage 603b is pushed up obliquely upward along the slide guide 602, the first stage 603a is pushed up obliquely upward along the slide guide 602 through the spring 604. When the first stage 603a is moved along the slide guide 602, the capillary head 205 is engaged with the hole 109a of the polymer block 109.

When the lever 610 is further rotated counterclockwise, the second stage 603b is pushed up obliquely upward along the slide guide 602. The force acts on the first stage 603a through the spring 604. However, the first stage 603a is no longer moved obliquely upward when the capillary head 205 is engaged with the hole 109a of the polymer block 109. Accordingly, the spring 604 is compressed. At this point, the force corresponding to compressive force of the spring 604 acts on the first stage 603a. That is, the capillary head 205 is engaged with the hole 109a of the polymer block 109 by the force corresponding to the compressive force of the spring 604.

The spring 604 needs to have sufficiently large elastic force, because the elastic force of the spring 604 supports at least the polymer block 109 which is of a movable portion, the syringe 108, check valve 110, polymer vessel 111, and positive electrode buffer vessel 112 which are connected to the polymer block 109 and, at the same time, the capillary head 205 is pressed into the hole 109a of the polymer block 109.

The hole 109a of the polymer block 109 is sealed by bringing the chamfering portion at the entrance of the hole 109a of the polymer block 109 into contact with the conical portion 205b of the capillary head 205. At this point, the inner diameter of the hole 205f of the capillary head 205 is decreased. Therefore, airtight is made between the hole 205f of the capillary head 205 and the capillary 101 arranged in hole 205f. A pressure of several mega-pascals is applied to the polymer when the polymer is introduced to the capillary 101. The pressure acts so as to separate the capillary head 205 from the polymer block 109. However, the capillary head 205 and the polymer block 109 are never separated from each other because the capillary head 205 and the polymer block 109 are pressed against each other by the force corresponding to the compressive force of the spring 604.

When the polymer block 109 is separated from the capillary head 205, the operator just has to rotate the lever 610 clockwise.

Figure 7:
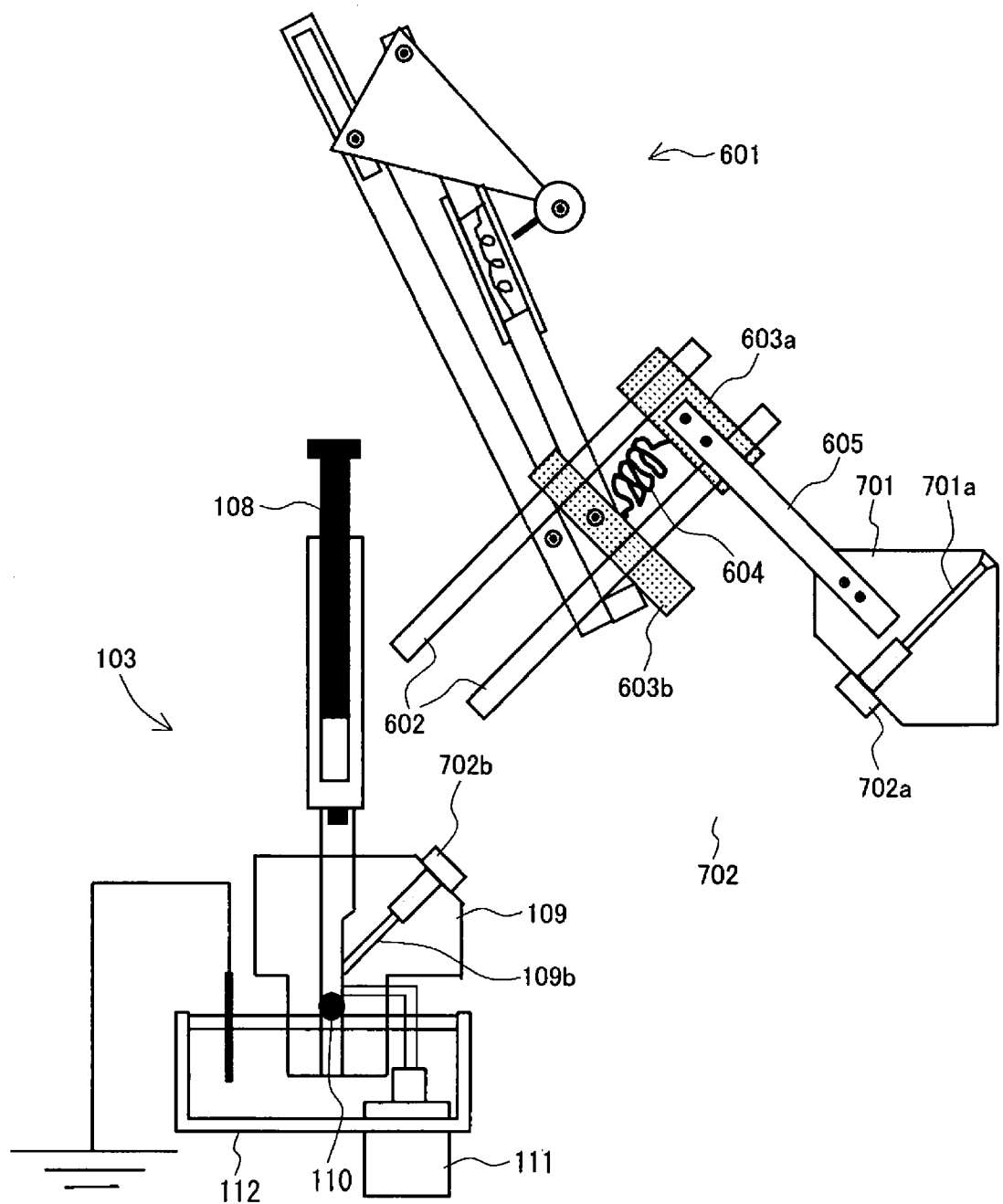
FIG. 7 shows a second example of the polymer filling unit of the capillary electrophoresis apparatus of the embodiment.

A structure of a second example of the polymer filling unit 103 of the capillary electrophoresis apparatus will be described below with reference to FIG. 7. An attachment portion 701 and a tube 702 are used in the second embodiment. A hole 701a into which the capillary head 205 is inserted is formed in the attachment portion 701. Engagement portions 702a and 702b are provided at both ends of the tube 702. One engagement portion 702a is attached into the hole 701a formed in the attachment portion 701, and the other engagement portion 702b is attached in a hole 109b formed in the polymer block 109. The flow path is formed from the hole 701a of the attachment portion 701 to the hole 109b of the polymer block 109. The capillary 101 is connected to the flow path in the polymer block 109 by inserting the capillary head 205 into the hole 701a of the attachment portion 701.

In the second example, the slide mechanism 601 is attached to the attachment portion 701. The configuration of the slide mechanism 601 of the second example may be similar to that of the slide mechanism 601 shown in FIG. 5. The slide guides 602 form the movement path of the first and second stages 603a and 603b. The movement path formed by the slide guides 602 is parallel to the axis line of the hole 701a formed in the attachment portion 701. The capillary head 205 is inserted into the hole 701a. That is, the hole 701a formed in the attachment portion 701 and the slide guide 602 are arranged in parallel with each other.

Because the first stage 603a is coupled to the attachment portion 701 through the block support member 605, the first stage 603a, the block support member 605, and the attachment portion 701 are integrally moved. That is, the first stage 603a, the block support member 605, and the attachment portion 701 are moved in parallel with the slide guide 602. In the second example, the polymer block 109 and the positive electrode buffer vessel 112 connected thereto are not moved.

Figure 5:
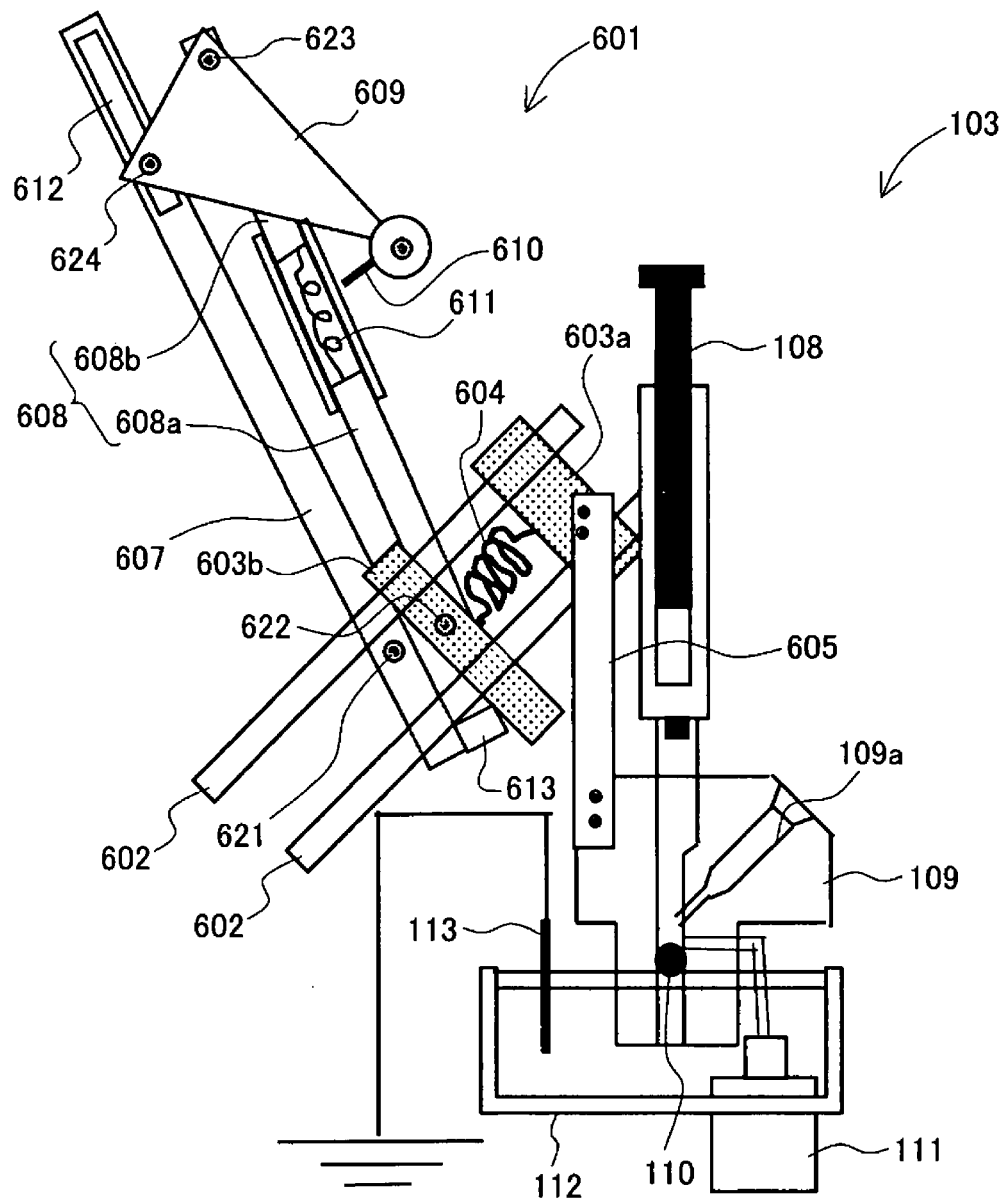
FIG. 5 shows a first example of a polymer filling unit of the capillary electrophoresis apparatus of the embodiment.

In the polymer filling unit 103 of the second example, the movable portion has a sufficiently smaller weight compared with the first example of FIG. 5. Accordingly, the elastic force of the spring 604 can be decreased compared with the first example of FIG. 5. The operation of rotating the lever becomes easy.

Figure 8:
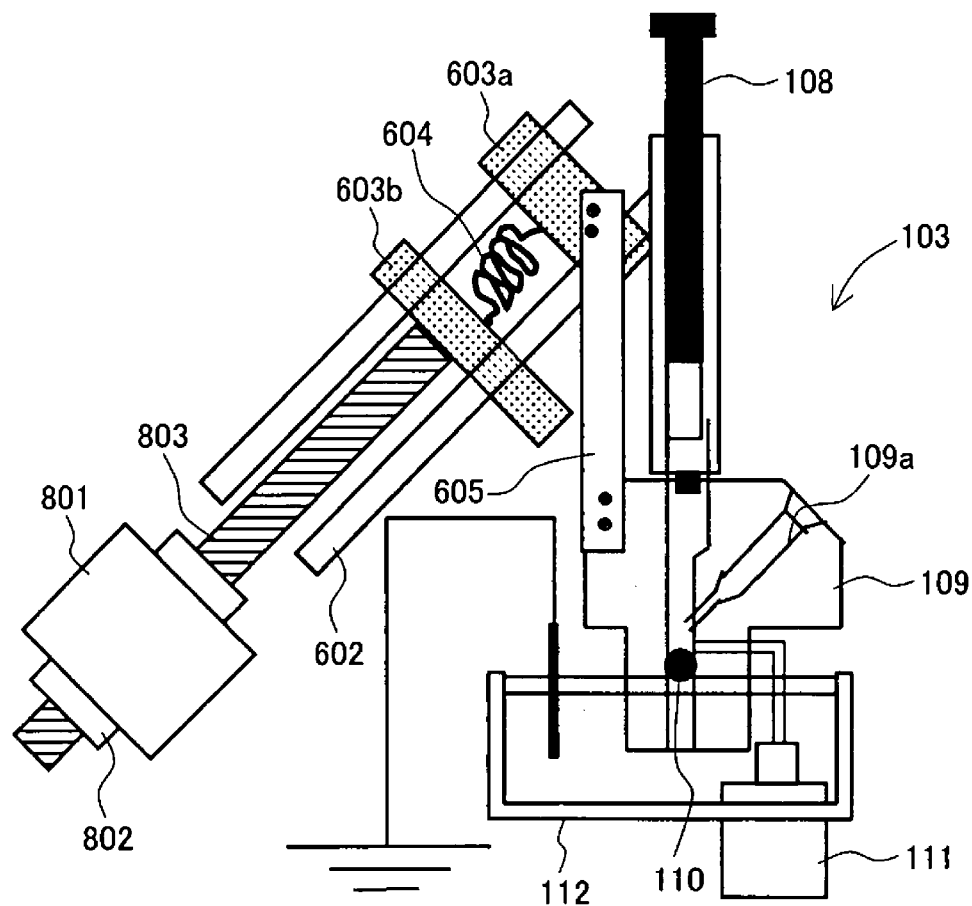
FIG. 8 shows a third example of the polymer filling unit of the capillary electrophoresis apparatus of the embodiment.

A structure of a third example of the polymer filling unit 103 of the capillary electrophoresis apparatus will be described below with reference to FIG. 8. In the third example, the slide mechanism 601 includes the two slide guides 602, the first stage 603a, the second stage 603b, the spring 604, the block support member 605, a motor 801, and a feed screw 803. A hollow hole is provided in a shaft 802 of the motor 801, and a female screw is formed in an inner surface of the hole. The feed screw 803 is attached into the hole. In the shaft 802 of the motor 801, a circumferentially-extended groove is formed in the inner surface of the hollow hole, and a bearing is attached between the groove and the feed screw 803. The front end of the feed screw 803 is connected to the second stage 603b.

When the shaft 802 of the motor 801 is rotated, the feed screw 803 is moved. As the feed screw 803 is moved, the second stage 603b is moved. As the second stage 603b is moved, the first stage 603a is also moved. Because the first stage 603a is coupled to the polymer block 109 through the block support member 605, the first stage 603a, the block support member 605, and the polymer block 109 are integrally moved. That is, the first stage 603a, the block support member 605, and the polymer block 109 are moved in parallel with the slide guide 602. The syringe 108, the check valve 110, the polymer vessel 111, and the positive electrode buffer vessel 112 are connected to the polymer block 109. These members and components are moved in parallel with the slide guide 602, along with the polymer block 109.

In the third example, the motor 801 is arranged such that the central axis line of the shaft 802 of the motor 801 is parallel to the slide guide 602. That is, the motor 801 is arranged such that the central axis line of the shaft 802 of the motor 801 is parallel to the axis line of the hole 109a in the polymer block 109.

When the capillary head 205 is inserted into the hole of the polymer block 109, the motor 801 is rotated such that the feed screw 803 is moved upward. When the capillary head 205 is separated from the hole of the polymer block 109, the motor 801 is rotated such that the feed screw 803 is moved downward.

A pressure of several mega-pascals is applied to the polymer when the polymer is introduced to the capillary 101. The force corresponding to the pressure acts so as to separate the capillary head 205 from the hole 109a of the polymer block 109. Accordingly, an electric current or voltage applied to the motor 801 is controlled such that the force for pushing up the second stage 603b with the feed screw 803 becomes about 10 MPa.

The elastic force of the spring 604 acts on the contact portion between the hole 109a of the polymer block 109 and the capillary head 205. Therefore, even if the motor 801 is turned off, or even if the feed screw 803 has a relief, or even if the seal is deformed, the airtightness is maintained between the hole 109a of the polymer block 109 and the capillary head 205 by the elastic force of the spring 604.

Figure 9A:
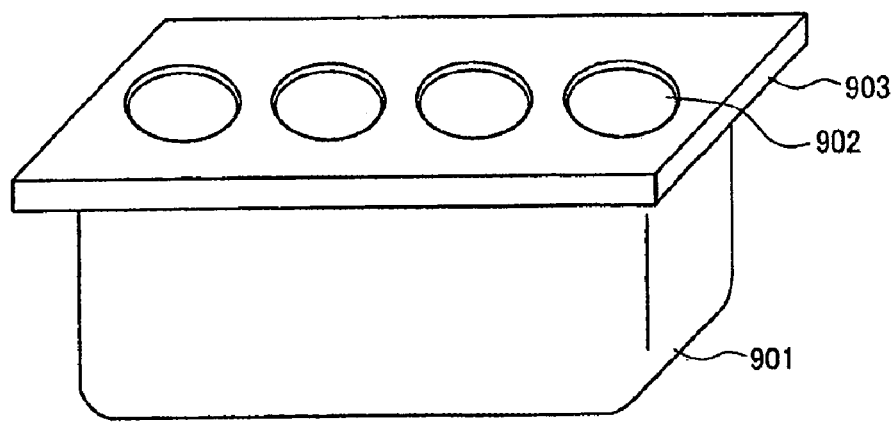
FIG. 9 shows an example of a buffer and sample storage vessel of the capillary electrophoresis apparatus of the embodiment.

A first example of the vessel of the capillary electrophoresis apparatus according to the embodiment of the invention will be described with reference to FIG. 9. A vessel 901 of the first example can simultaneously store the sample and the buffer. It is assumed that the vessel 901 is vertically moved by the movable stage 107 of the conveyer 115. As shown in FIG. 9A, the vessel 901 includes plural recesses 902, and a collar 903 is formed at the upper end of the vessel 901.

Figure 9B:
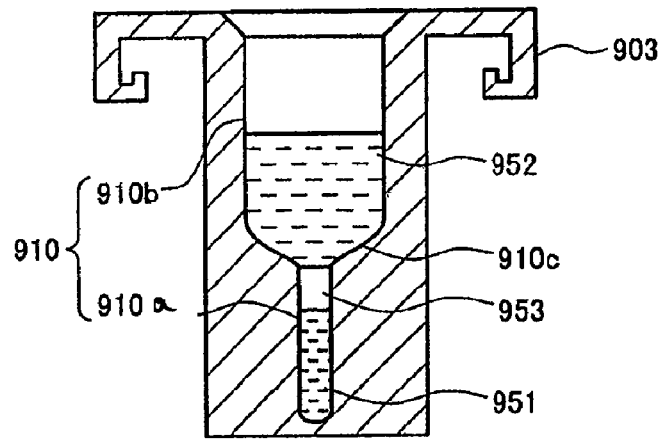

FIG. 9B shows a first example of the recess. A recess 910 of the example includes a lower-side sample storage unit 910a and an upper-side buffer storage unit 910b, and the sample storage unit 910a and the buffer storage unit 910b are continuously connected. The sample storage unit 910a has a cross section smaller than that of the buffer storage unit 910b. Accordingly, a shoulder 910c is formed at a boundary between the sample storage unit 910a and the buffer storage unit 910b. For example, the sample storage unit 910a may have the circular cross section whose inner diameter is 2 mm while the buffer storage unit 910b has the circular cross section whose inner diameter is 8 mm.

A method of using the vessel will be described. The operator injects a sample 951 into the sample storage unit 910a. The sample 951 is injected such that the sample storage unit 910a is not filled with the sample 951, but a space remains in the upper-end portion. Then, a buffer 952 is injected. At this point, an air layer 953 is formed between the sample 951 and the buffer 952. The contact surface between the buffer 952 and the air layer 953 is retained by surface tension, so that the buffer 952 never drops on the sample storage unit 910a. Accordingly, the sample 951 and the buffer 952 are stored in the vessel while separated from each other.

The vessel 901 in which the sample 951 and the buffer 952 are stored is arranged below the capillary negative-electrode end. The vessel 901 is raised by the movable stage 107 of the conveyer 115. The capillary negative-electrode end passes through the buffer 952 and enters the sample 951, and in this state of things, the sample 951 is introduced into the capillary 101. Then, the vessel 901 is raised by the movable stage 107 of the conveyer 115, which arranges the capillary negative-electrode end in the buffer 952. In this state of things, the electrophoresis is performed. Alternatively, the capillary 101 may be moved instead of the movement of the vessel 901 with the movable stage 107 of the conveyer 115.

Figure 9C:
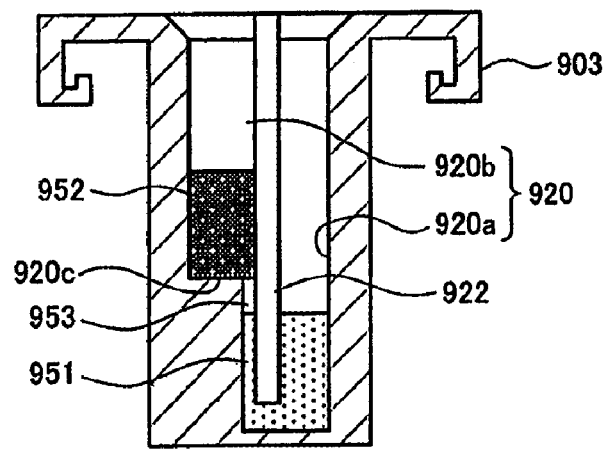

FIG. 9C shows a second example of the recess. A recess 920 of the second example includes an upper-side portion and a lower-side portion, and the lower-side portion is formed in the bottom surface of the upper-side portion. A shoulder is formed at a boundary between the upper-side portion and the lower-side portion. A partition wall 922 is provided to divide the recess into two portions. The partition wall 922 is extended from an opening of the recess to near the bottom surface of the lower-side portion. A gap is provided between the lower end of the partition wall 922 and the bottom surface of the lower-side portion, and a gap is also provided between the partition wall 922 and an inner wall of the lower-side portion. Accordingly, a space is continuously formed in the recess.

In the second example, a sample storage unit 920a is formed by the lower-side portion, and a buffer storage unit 920b is formed by the upper-side portion and the partition wall 922.

A method of using the vessel will be described. The operator injects a sample 951 into the sample storage unit 920a. The sample 951 is injected such that the sample storage unit 920a is not filled with the sample 951. The sample 951 passes between the lower end of the partition wall 922 and the bottom surface of the lower-side portion, and the sample 951 proceeds into the gap between the partition wall 911 and the inner wall of the lower-side portion. Then, the buffer 952 is injected into the buffer storage unit. At this point, the air layer 953 is formed between the sample 951 and the buffer 952, in the gap between the partition wall and the inner wall of the lower-side portion. The contact surface between the buffer 952 and the air layer 953 is retained by the surface tension, so that the buffer 952 never drops on the sample storage unit 920a. Accordingly, the sample 951 and the buffer 952 are stored in the vessel while separated from each other.

The vessel 901 in which the sample 951 and the buffer 952 are stored is arranged below the capillary negative-electrode end. The vessel 901 is raised by the movable stage 107 of the conveyer 115. The capillary negative-electrode end passes through the buffer 952, the capillary negative-electrode end passes through the gap between the partition wall 922 and the inner wall of the lower-side portion, and the capillary negative-electrode end enters the sample 951. In this state of things, the sample 951 is introduced into the capillary 101. Then, the vessel 901 is raised by the movable stage 107 of the conveyer 115, which arranges the capillary negative-electrode end in the buffer 952. In this state of things, the electrophoresis is performed. Alternatively, the capillary 101 may be moved instead of the movement of the vessel 901 with the movable stage 107 of the conveyer 115.

A second example of the vessel of the capillary electrophoresis apparatus of the invention will be described with reference to FIG. 10. The vessel of the second example can simultaneously store the sample and the buffer. It is assumed that the vessel is vertically moved by the movable stage 107 of the conveyer 115.

FIG. 10A shows a configuration of a transverse section of the vessel of the second example, and FIG. 10B shows longitudinal section taken along a line B-B of FIG. 10A. A vessel 1001 of the second example includes an upper-side sample storage unit 1010 and a lower-side buffer storage unit 1020, and has a structure where they are stacked. The bottom of the sample storage unit 1010 is formed of a film 1011. As shown in FIG. 10B, a film 1012 may further be provided below the film 1011. The film 1012 is obliquely provided with respect to a horizontal plane.

Partition units 1013 are provided in the sample storage unit 1010, and partition units 1023 are provided in the buffer storage unit 1020. The sample storage unit 1010 and the buffer storage unit 1020 can be respectively divided into plural sections by providing the partition units. The partition unit 1013 of the sample storage unit 1010 and the partition unit 1023 of the buffer storage unit 1020 are provided at corresponding positions. Accordingly, each section of the buffer storage unit 1020 is arranged below each section of the sample storage unit 1010.

When the vessel is provided to a user, the buffer may previously be encapsulated in the buffer storage unit 1020. The user stores the sample in the sample storage unit 1010 at the point of use. When the vessel is provided to the user, the sample and the buffer may be in an empty state. In such cases, an injection hole 1021 is provided in a sidewall of the vessel to inject the buffer.

The vessel of the second example may be formed out of polypropylene. The film 1011 and 1012 are made of polyethylene or polyethylene terephthalate. The film 1011 and 1012 have a thickness of 0.07 mm, and the film 1011 and 1012 are thermally welded to the vessel.

A method of using the vessel will be described. The operator injects a sample 1051 into each recess of the sample storage unit 1010. Then, a buffer 1052 is injected into each recess of the buffer storage unit 1020 through the injection hole 1021. This process is not required in the case where the buffer 1052 is previously encapsulated.

The vessel 1001 in which the sample 105 1 and the buffer 1052 are stored is arranged below the capillary negative-electrode end. The vessel 1001 is raised by the movable stage 107 of the conveyer 115. The capillary negative-electrode end enters the sample 1051, and in this state of things, the sample 1051 is introduced into the capillary 101. Then, the vessel 1001 is raised by the movable stage 107 of the conveyer 115. Therefore, the capillary negative-electrode end passes through the sample 1051, the capillary negative-electrode end breaks through the films 1011 and 1012 and the capillary negative-electrode end is arranged in the buffer 1052. In this state of things, the electrophoresis is performed. Alternatively, the capillary 101 may be moved instead of the movement of the vessel 1001 with the movable stage 107 of the conveyer 115.

When the capillary negative-electrode end breaks through the film 1011, the sample 1051 possibly leaks from the hole of the film 1011. However, the leaked sample flows along the obliquely provided film 1012, and the sample never enters the buffer 1052 located on the lower side. In the case of the polyethylene film 1011, when the capillary negative-electrode end is stuck into the film 1011, the hole contracts by frictional heat generated by sticking the capillary negative-electrode end into the film 1011, and the film 1011 adheres tightly to the capillary. Therefore, the sample never leaks from the hole.

When the capillary negative-electrode end proceeds in a liquid surface of the buffer 1052, sometimes the buffer 1052 is splashed. The splash of the buffer 1052 is prevented by the partition units 1023 provided in the buffer storage unit 1020.

Figure 10:
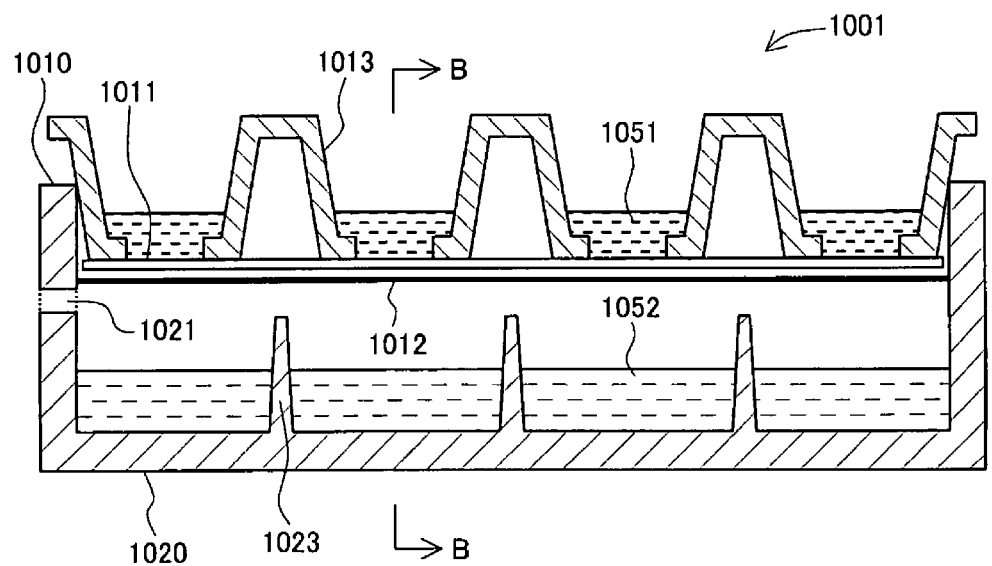
FIG. 10 shows another example of the buffer and sample storage vessel of the capillary electrophoresis apparatus of the embodiment.
Figure 10:
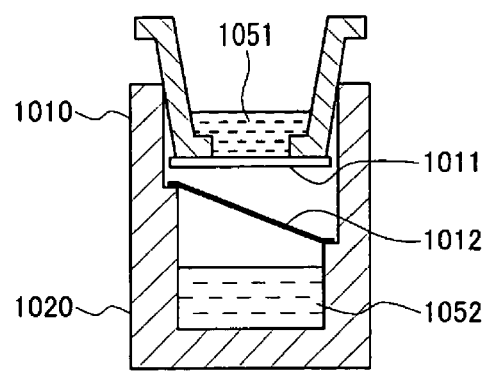

In the example of FIG. 10, the vessel includes the upper-side sample storage unit 1010 and the lower-side buffer storage unit 1020. However, at least three storage units may be provided in the vessel. The case in which a distilled water storage unit in which distilled water is stored is provided above the sample storage unit 1010 will be described below. As with the bottom of the sample storage unit 1010, the bottom of the distilled water storage unit is formed out of a film. A film is obliquely provided below the distilled water storage unit.

A method of using the vessel having the above three-stage storage unit will be described. The vessel in which the distilled water, the sample 1051, and the buffer 1052 are stored respectively are arranged below the capillary negative-electrode end. When the vessel is raised by the movable stage 107 of the conveyer 115, the capillary negative-electrode end enters the distilled water, which washes the capillary negative-electrode end. Then, when the vessel is further raised by the movable stage 107 of the conveyer 115, the capillary negative-electrode end breaks through the film and enters the sample 1051. In this state of things, the sample 1051 is introduced into the capillary 101. The vessel is further raised by the movable stage 107 of the conveyer 115. Therefore, the capillary negative-electrode end passes through the sample 1051 to break through the films 1011 and 1012, and the capillary negative-electrode end is arranged in the buffer 1052. In this state of things, the electrophoresis is performed. Alternatively, the capillary 101 may be moved instead of the movement of the vessel with the movable stage 107 of the conveyer 115.

The vessel is lowered by the movable stage 107 of the conveyer 115, when the electrophoresis is performed for the sample stored in the adjacent recess after the electrophoresis is ended for the sample stored in one recess of the sample storage unit 1010. When the capillary negative-electrode end disengages from the vessel, the vessel is horizontally moved by the movable stage 107 of the conveyer 115. Then,as described above, the vessel is raised by the movable stage 107 of the conveyer 115.

As described above, when the capillary negative-electrode end is stuck in the film 1011, the hole contracts and the film 1011 adheres tightly to the capillary, so that the sample never leaks from the hole. However, sometimes the remaining sample is removed from the sample storage unit 1010. Therefore, a wedge-shape member may be attached to the capillary negative-electrode end 206. The wedge-shape member is attached at a slightly retreating position from the front end of the capillary negative-electrode end 206, or attached to the hollow electrode.

When the vessel is raised by the movable stage 107 of the conveyer 115, the capillary negative-electrode end enters the sample 1051. In this state of things, the sample is introduced into the capillary 101. Then, the vessel is raised by the movable stage 107 of the conveyer 115. Therefore, the capillary negative-electrode end passes through the sample 1051 and breaks through the film 1011 which is of the bottom of the sample storage unit 1010. When the capillary negative-electrode end breaks through the film 1011, the wedge-shape member enlarges the hole. When the wedge-shape member enlarges the hole of the film 1011, the sample flows out from the hole. The sample flows down along the obliquely provided film 1012.

The capillary negative-electrode end and the wedge-shape member break through the obliquely provided film 1012 and enter the buffer. In this state of things, the electrophoresis is performed.

Figure 11:
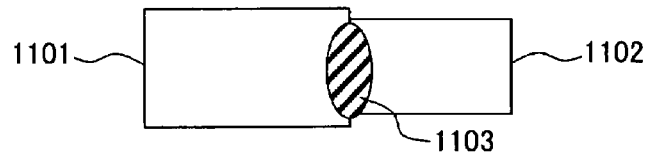
FIG. 11 shows that a temperature is unstable at a boundary portion between two temperature control units in a capillary temperature control device of the capillary electrophoresis apparatus.
Figure 11:
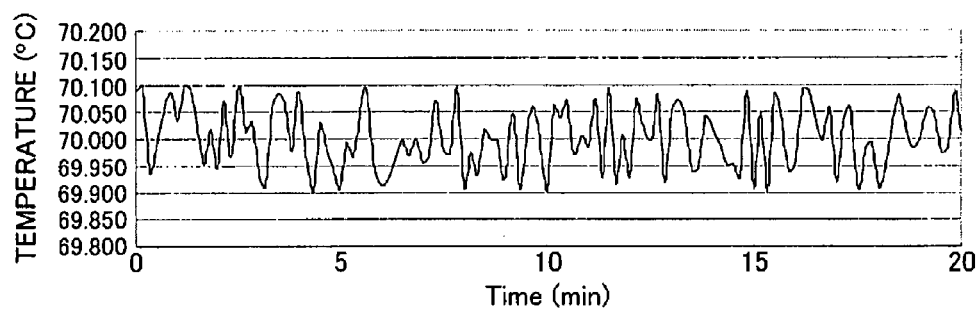
Figure 11:
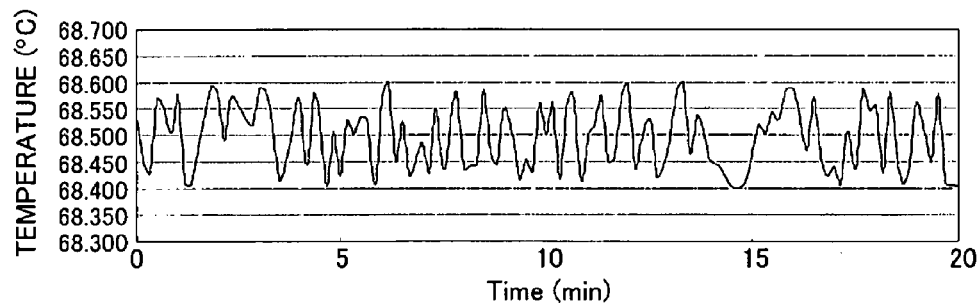
Figure 11:
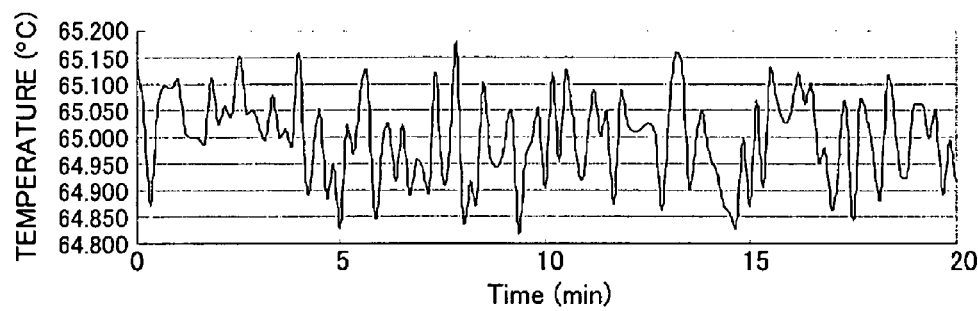

The temperature control of the capillary will be described with reference to FIG. 11. During the electrophoresis, the electric current is passed through the separation medium in the capillary, and heat is generated from the inside of the capillary. The temperature of the capillary fluctuates by the heat generated from the capillary, which possibly deteriorates result of analysis. Therefore, the temperature control unit is provided in the capillary to keep the capillary at a constant temperature.

FIG. 11A shows the case in which the temperature control unit is provided in each region of the capillary. Each temperature control unit has a temperature control element of itself, and the temperature control unit controls the temperature based on the temperature control element of itself. That is, each temperature control unit independently controls the temperature. In such cases, temperature change is increased by an influence of the two temperature control units at a boundary portion 1103 between adjoining temperature control units 1101 and 1102.

FIG. 11B shows a temperature of the first temperature control unit 1101, FIG. 11C shows a temperature of the second temperature control unit 1102, and FIG. 11D shows a temperature of the boundary portion 1103 between the temperature control units 1101 and 1102.

The heat flows into the boundary portion 1103 between the two temperature control units from both the first temperature control unit 1101 and the second temperature control unit 1102. Accordingly, the temperature change in the boundary portion 1103 becomes a value into which the temperature change of the first temperature control unit 1101 and the temperature change of the second temperature control unit 1102 are added. For example, when a standard deviation is 0.06° C. in the temperatures of the first and second temperature control units 1101 and 1102, the standard deviation becomes 0.09° C. in the boundary portion 1103.

This shows that the temperature is unstable in the boundary portion between the two temperature control units compared with the temperature control units. That is, when the plural temperature control units are provided in the capillary to independently operate each temperature control unit, the capillary temperature becomes unstable in the boundary portion between the temperature control units, which possibly deteriorates the result of analysis.

Figure 12:
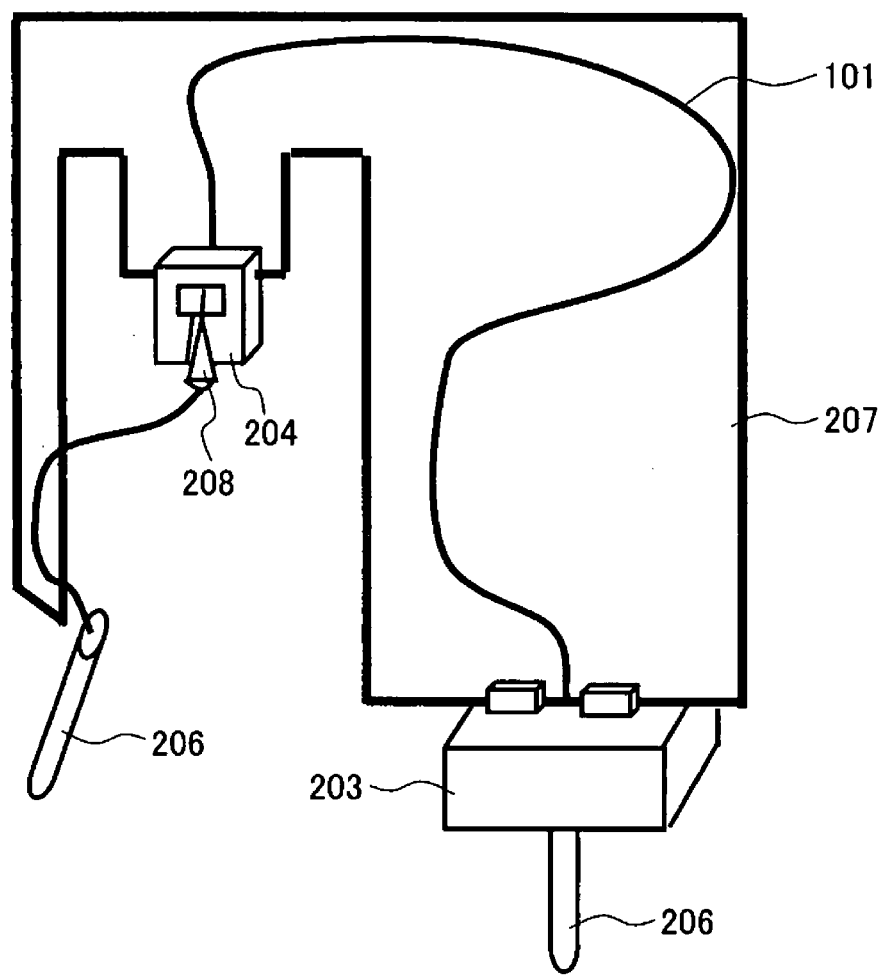
FIG. 12 shows a second example of the capillary array of the capillary electrophoresis apparatus of the embodiment.

FIG. 12 shows the detailed second example of the capillary array 102 of the capillary electrophoresis apparatus. The capillary head 205 is provided at one end of the capillary 101, and the capillary negative-electrode end 206 is provided at the other end. The capillary 10 and the capillary head 205 may be fixed to each other with the bonding agent. The metal hollow electrode is attached to the load header 203. The capillary negative-electrode end 206 pierces through the hollow electrode and the capillary negative-electrode end 206 is projected from the hollow electrode. The capillary 101 is fixed onto the array sheet 207. The optical detection unit includes the conical lens 208 and the reference base 204. The detection portion of the capillary 101 is held on the reference base 204. The detection portion of the capillary 101 is irradiated with the excitation light which is emitted from the light source, through the conical lens 208.

Figure 13:
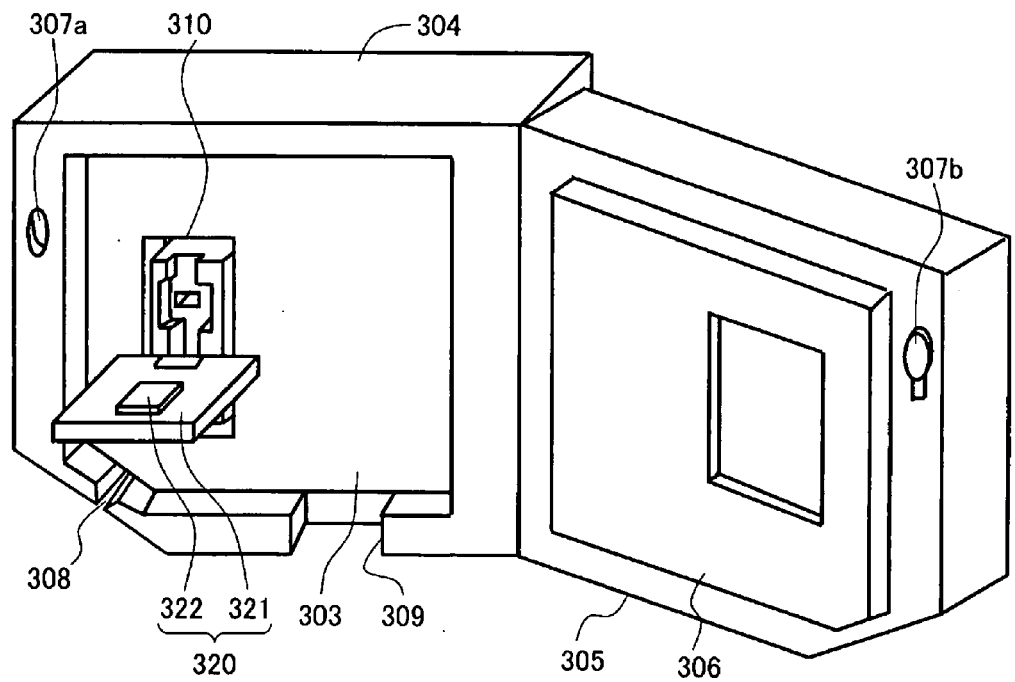
FIG. 13 shows another example of the thermostatic device of the capillary electrophoresis apparatus of the embodiment.
Figure 13:
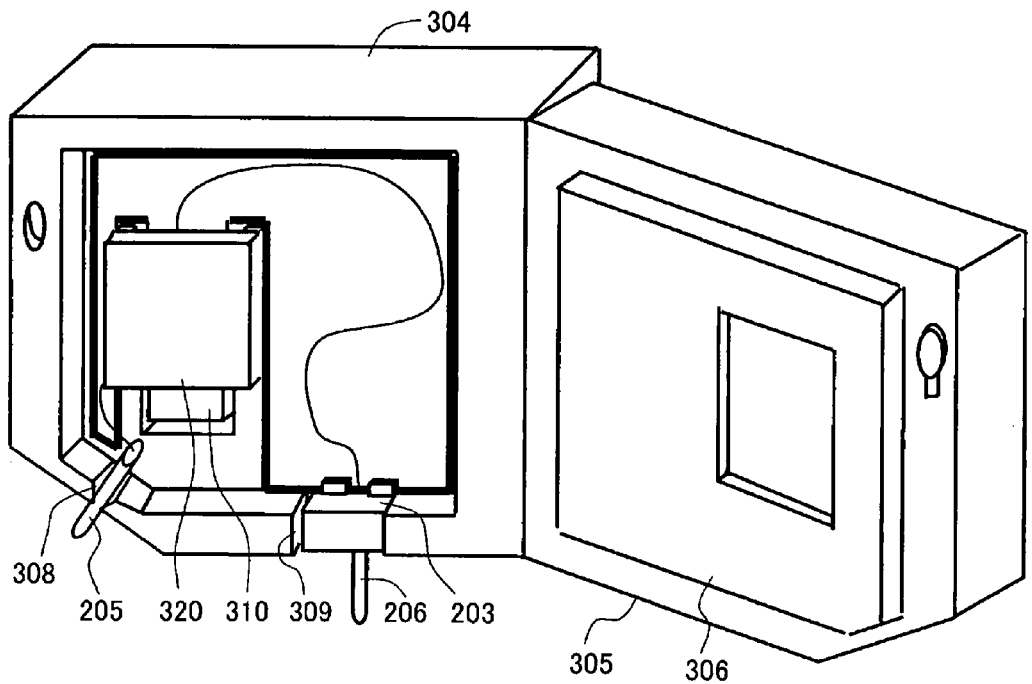

FIG. 13 shows an example of the thermostatic device 106. As shown in FIG. 13A, the thermostatic device 106 includes the main body frame 304 and the door frame 305. The temperature control member 303 is placed in the main body frame 304. The hole is provided in the temperature control member 303, and the accurately-formed optical detection unit holder 310 is arranged in the hole.

The optical detection unit holder cover 320 is coupled to the optical detection unit holder 310 with a hinge to cover the optical detection unit holder 310 therewith. The optical detection unit holder cover 320 includes a temperature propagation member 321 and a reference base pressing rubber 322. The capillary-header groove 308 and the load-header notch portion 309 are formed in the main body frame 304. The capillary array pressing sponge 306 is attached to the door frame 305.

FIG. 13B shows the state in which capillary array 102 is attached into the main body frame 304. The array sheet 207 is arranged on the temperature control member 303. The capillary head 205 is inserted into the capillary-header groove 308 of the main body frame 304. The load header 203 is inserted into the load-header notch portion 309 of the main body frame 304. The reference base 204 of the capillary array 102 is engaged in the reference-base groove of the optical detection unit holder 310.

Then, the optical detection unit holder cover 320 is closed. The reference base 204 of the irradiation and detection unit 120 is pressed by the reference base pressing rubber 322. Therefore, the movement of the reference base 204 of the irradiation and detection unit 120 is prevented during the electrophoresis. The temperature propagation member 321 of the optical detection unit holder cover 320 is brought into contact with the temperature control member 303. Therefore, the heat is transferred from the temperature control member 303 to the detection portion of the capillary 101 through the temperature propagation member 321.

When the capillary array 102 is attached to the main body frame 304, the door frame 305 is closed. The capillary array pressing sponge 306 holds the array sheet 207 on the temperature control member 303, which securely brings the capillary 101 into contact with the temperature control member 303. Accordingly, in the example, the capillary 101 is always kept at a constant temperature by the heat from the temperature control member 303.

The lock 307a of the main body frame 304 is engaged with the lock 307b of the door frame 305. The electrophoresis is performed while the main body frame 304 and the door frame 305 are closed.

Figure 14:
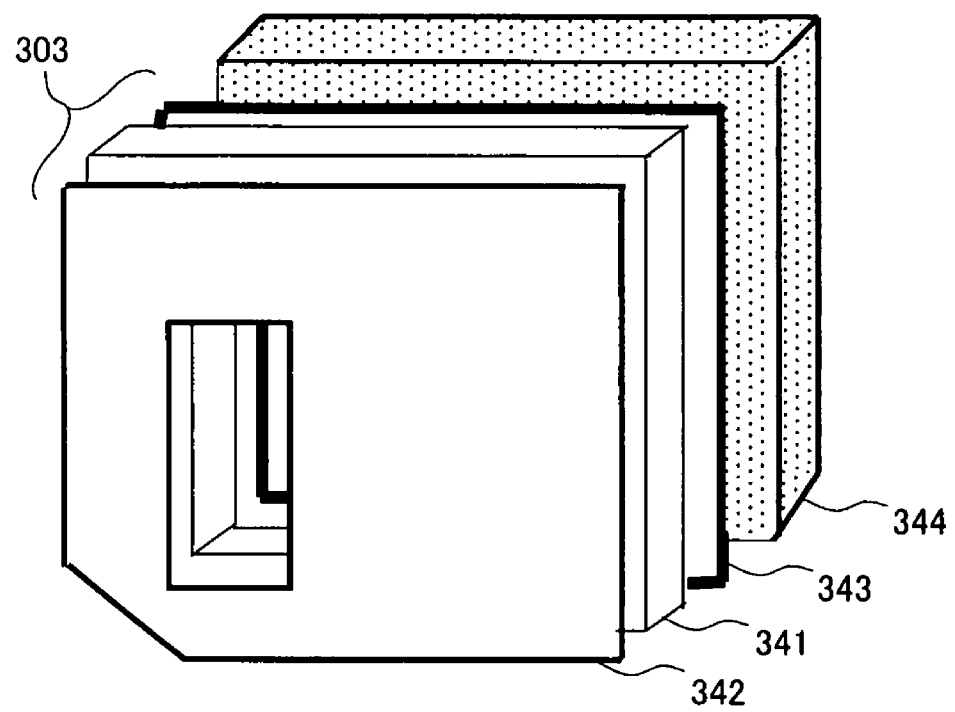
FIG. 14 shows structures of a temperature control member and a heat insulation material in the thermostatic device of the capillary electrophoresis apparatus of the embodiment.

FIG. 14 shows a structure of the temperature control member 303. The temperature control member 303 is formed of a three-layer structure, which consists of a heat sink plate 341 located in the middle, a heat radiation sheet 342 located inside, and a heater 343 located outside. The heater 343 is covered with a heat insulation material 344 so as to come into contact with an outside air. A temperature sensor is provided in the temperature control member 303. The temperature sensor detects the temperature of the temperature control member 303, and a feedback circuit controls the heater 343.

In the example, the temperature sensor, the feedback circuit, and the heater 343 constitute the temperature control device. The temperature control device keeps the temperature control member 303 at a constant temperature. In the example, the temperature control device provided in the temperature control member 303 controls not only the temperature of the capillary but also the temperatures of the irradiation and detection unit 120, optical detection unit holder 310, and optical detection unit holder cover 320. The individual temperature control device is not provided in the irradiation and detection unit 120, the optical detection unit holder 310, and the optical detection unit holder cover 320. Thus, in the example, because the single temperature control device controls the temperature of the capillary electrophoresis apparatus, an error caused by the temperature fluctuation in the boundary portion shown in FIG. 11 can be eliminated.

The thermostatic device 106 can control the temperature in the range of an ambient temperature to 70 degrees Celsius. Accordingly, it is necessary that the material of the member constituting the thermostatic device 106 has a heat-resisting property up to about 70 degrees Celsius. The main body frame 304 and the door frame 305 are formed of PPO (polyphenylene ether resin) having the heat-resisting property, and the main body frame 304 and the door frame 305 are formed by low foam moulding to enhance heat insulation effect. The capillary array pressing sponge 306 is formed of silicone sponge having both the high heat-resisting property and a small compression permanent strain.

In the case where the temperature fluctuates partially in the thermostatic device 106, it is necessary that the heat sink plate 341 has a function of rapidly absorbing the fluctuation to keep the thermostatic device 106 at a constant temperature. Therefore, desirably the heat sink plate 341 is made of a material having a large coefficient of thermal conductivity, such as metal, particularly copper and aluminum.

In addition to the heat-resisting property, it is necessary that the heat radiation sheet 342 is brought into contact with the capillary 101 to absorb the heat generated from the capillary 101. Additionally, it is desirable that a mark of the capillary 101 is not left in the heat radiation sheet 342 by the contact with the capillary 101. Therefore, preferably the heat radiation sheet 342 is made of a material having both the large coefficient of thermal conductivity and the small compression permanent strain. Silicone rubber having high thermal conductivity (coefficient of thermal conductivity ranges from 1 to 3 W/mK) can be cited as an example of the material satisfying the conditions.

Because the temperature sensor provided in the temperature control member 303 detects the temperature of the portion which is brought into contact with the temperature control member 303, desirably there is no temperature difference in the temperature control member 303 as a whole. Therefore, an interval between heating wires of the heater 343 becomes dense in a peripheral portion of the heat sink plate 341, and the interval becomes coarse in other portions. Thus, the whole of the temperature control member 303 becomes a constant temperature by adjusting the density of the heating wire of the heater 343, which allows the temperature sensor to detect the real temperature of the temperature control member 303.

The heat flow in the thermostatic device of the example will be described. The heat is transferred from the heater 343 to the heat sink plate 341, and the heat is further transferred to the heat radiation sheet 342. The heat transferred to the heat radiation sheet 342 is transferred to the temperature propagation member 321 of the optical detection unit holder cover 320. The heat is further transferred to the reference base pressing rubber 322, the reference base 204 of the irradiation and detection unit 120, and the detection portion of the capillary 101. Therefore, the temperature is increased in the detection portion of the capillary 101.

Accordingly, the temperature propagation member 321 and reference base pressing rubber 322 of the optical detection unit holder cover 320 are suitably made of a material having the high thermal conductivity. The high heat-resisting property and the small compression permanent strain are also required for the reference base pressing rubber 322. Therefore, preferably the reference base pressing rubber 322 may be formed of silicone rubber having the high thermal conductivity (coefficient of thermal conductivity ranges from 1 to 3 W/mK). The temperature propagation member 321 is desirably formed of metal such as aluminum and copper.

When the temperatures are increased in the reference base 204 of the irradiation and detection unit 120 and the detection portion of the capillary 101, the temperature difference is generated between the side which is in contact with the reference base 204 of the irradiation and detection unit 120 and the side which is in contact with the other optical detection unit exposed to the outside air in the optical detection unit holder 310. Due to the temperature difference, the heat is dissipated from the reference base 204 of the irradiation and detection unit 120 to the outside of the thermostatic device 106 through the optical detection unit holder 310. A heat quantity dissipated from the reference base 204 of the irradiation and detection unit 120 to the outside of the thermostatic device 106 depends on the temperature difference between the ambient temperature and that of the reference base 204 of the irradiation and detection unit 120. As the fluctuation in the dissipated heat quantity is increased, the temperature of the reference base 204 of the irradiation and detection unit 120 fluctuates, and the temperature becomes unstable in the detection portion of the capillary 101. When the dissipated heat quantity is decreased, the temperature is stabilized in the detection portion of the capillary 101. The following two examples are shown as means for decreasing the dissipated heat quantity.

In a first example of the means for decreasing the dissipated heat quantity, the optical detection unit holder 310 is made of the material having the coefficient of thermnal conductivity smaller than that of the temperature propagation member 321 of the optical detection unit holder cover 320. The heat is transferred from the temperature control member 303 to the reference base 204 of the irradiation and detection unit 120 and the detection portion of the capillary 101 through the optical detection unit holder cover 320. However, because the optical detection unit holder 310 has the small coefficient of thermal conductivity, the small heat quantity is transferred from the optical detection unit holder cover 320 to the optical detection unit holder 310. Accordingly, the small heat quantity is dissipated from the optical detection unit holder 310 to the outside air. The temperature propagation member 321 of the optical detection unit holder cover 320 can be maintained at the temperature close to the temperature of the temperature control member 303, so that the reference base 204 of the irradiation and detection unit 120 and the detection portion of the capillary 101 can be maintained at proper temperatures.

In the example, preferably the optical detection unit holder 310 is made of PPS (polyphenylene sulfide resin) in which glass fiber is mixed. PPS with the mixed glass fiber has the coefficient of thermal conductivity of about 0.2 W/mK which is sufficiently smaller than that of the temperature propagation member 321 of the optical detection unit holder cover 320, and PPS with the mixed glass fiber also has the excellent heat-resisting property and strength.

In a second example of the means for decreasing the dissipated heat quantity, the optical system which is in contact with the optical detection unit holder 310 is made of the material having the coefficient of thermal conductivity smaller than that of the optical detection unit holder 310. The heat is transferred from the temperature control member 303 to the temperature propagation member 321 of the optical detection unit holder cover 320, and the heat is further transferred to the reference base 204 of the irradiation and detection unit 120 and the detection portion of the capillary 101. However, because the optical system which is in contact with the optical detection unit holder 310 has the small coefficient of thermal conductivity, the small heat quantity is transferred from the optical detection unit holder 310 to the optical system which is in contact therewith. Accordingly, the small heat quantity is dissipated from the optical system which is in contact with the optical detection unit holder 310 to the outside air, so that the reference base 204 of the irradiation and detection unit 120 and the detection portion of the capillary 101 can be maintained at proper temperatures.

Figure 15:
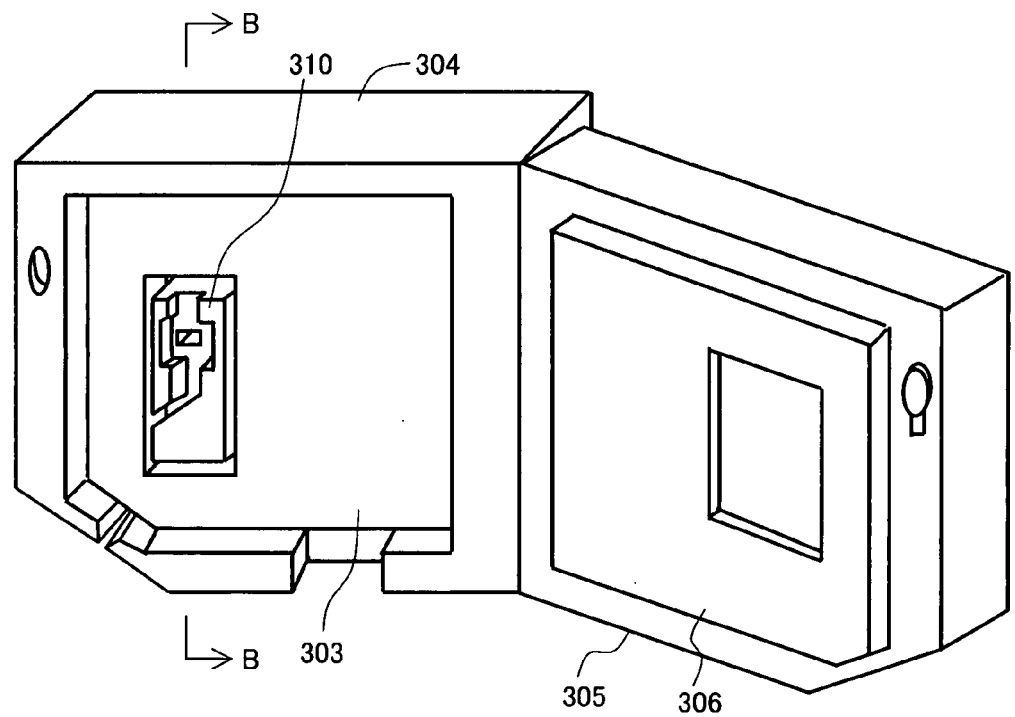
FIG. 15 shows a structure in which an optical detection unit holder is attached in the thermostatic device of the capillary electrophoresis apparatus of the embodiment.
Figure 15:
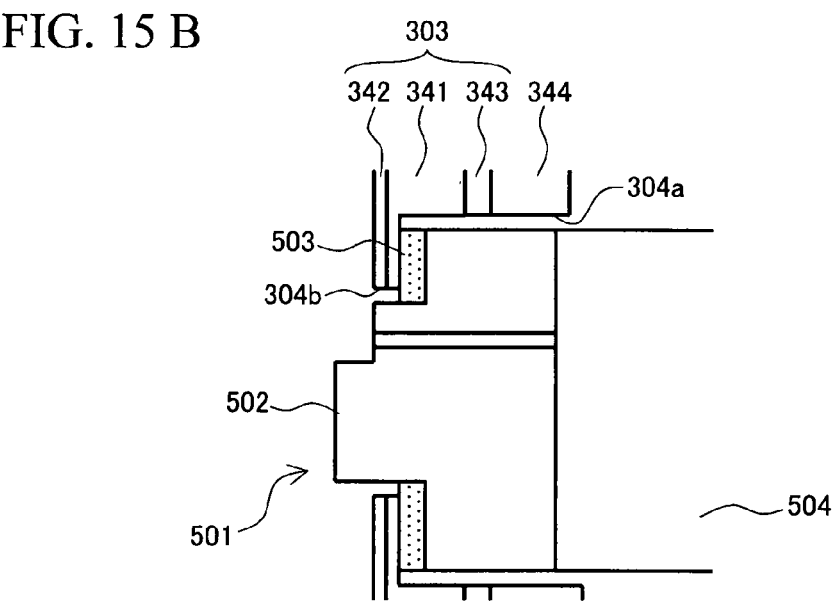

The attachment structure of the optical detection unit holder 310 will be described with reference to FIG. 15. FIG. 15A shows the state in which the optical detection unit holder cover 320 is removed. FIG. 15B shows a sectional structure taken on a line B-B of the thermostatic device of FIG. 15A. The main body frame 304 includes the temperature control member 303 and a heat insulation material 344. The temperature control member 303 includes the three-layer structure, which consists of the heat sink plate 341 located in the middle, the heat radiation sheet 342 located inside, and the heater 343 located outside. A hole 304a is provided in the main body frame 304. The hole 304a pierces through the temperature control member 303 and the heat insulation material 344. In the hole 304a, a circumferential projection 304b is formed around an opening located on the inside.

The optical detection unit holder 501 of the example includes the reference base holder 502 and the temperature propagation rubber 503, and the optical detection unit holder 501 is arranged in the hole 304a of the temperature control member 303 of the main body frame 304. The heat sink plate 341 of the temperature control member 303 is in contact with the temperature propagation rubber 503. A heat propagation path is formed between the temperature control member 303 and the optical detection unit holder 501 by the temperature propagation rubber 503. In the example, the temperature propagation member 321 of the optical detection unit holder cover 320 is not required.

The heat is transferred from the heater 343 to the temperature propagation rubber 503 through the heat sink plate 341. The heat is further transferred from the temperature propagation rubber 503 to the reference base holder 502. The heat transferred to the reference base holder 502 is transferred to the reference base 204 of the irradiation and detection unit 120 held by the reference base holder 502. Therefore, the detection portion of the capillary 101 is heated.

The temperature propagation rubber 503 and the reference base holder 502 are formed of the material having the large heat conductivity. The high heat-resisting property and the small compression permanent strain are also required for the temperature propagation rubber 503. Therefore, preferably the temperature propagation rubber 503 is made of silicone rubber having the high thermal conductivity (coefficient of thermal conductivity ranges from 1 to 3 W/mK). Preferably the reference base holder 502 is formed of metal such as aluminum and copper.

In the example, the optical system 504 which is in contact with the optical detection unit holder 501 is made of the material having the coefficient of thermal conductivity smaller than that of the optical detection unit holder 501. The heat is transferred from the temperature control member 303 to the reference base holder 502 through the temperature propagation rubber 503. However, because the optical system 504 has the small coefficient of thermal conductivity, the small heat quantity is transferred from the reference base holder 502 to the optical system 504. Accordingly, the small heat quantity is dissipated from the optical system 504 to the outside air, so that the reference base 204 of the irradiation and detection unit 120 and the detection portion of the capillary 101 can be maintained at proper temperatures.

In the example, the components of optical system 504 which is in contact with the optical detection unit holder 501 may be made of PPS (polyphenylene sulfide resin) in which the glass fiber is mixed.

The invention is not limited to the above embodiments, but it is understood for those skilled in the art that various changes can be made without departing from the scope of the following claims.

What is claimed is:

1. A capillary electrophoresis apparatus comprising:
a capillary array having a capillary with which a migration medium can be filled and a capillary head which is provided at one end of the capillary;
an optical detection unit which optically detects a sample electrically migrated in the capillary; and
a migration medium filling mechanism which fills the capillary with a migration medium,
wherein the capillary head is held at a predetermined position and the migration medium filling mechanism has a block including a hole which is engaged with the capillary head, a syringe which fills the capillary with a migration medium through the hole, and a slide mechanism which moves the block along a path parallel to a central axis line of the capillary head such that the central axis line of the capillary head is aligned with a central axis line of the hole.

2. The capillary electrophoresis apparatus according to claim 1, wherein the slide mechanism has two slide guides which are arranged in parallel to each other, first and second stages which are movable along the slide guide, a spring which connects the first and second stages, a block support member which connects the first stage to the block, and a drive mechanism which drives the second stage along the slide guide.

3. The capillary electrophoresis apparatus according to claim 2, wherein the drive mechanism has a feed screw which is connected to the second stage and a motor which moves the feed screw along the axis line direction.

4. The capillary electrophoresis apparatus according to claim 2,
wherein the drive mechanism has a rotatable lever,
a triangular member which is connected to said lever at a first vertex of the triangular member and the triangular member pivots along with said lever,
a first rod which is connected to a second vertex of the triangular member and is rotatably attached to the chassis of the capillary electrophoresis apparatus by a first pin and pivots about the first pin,
a second rod, comprising a first and second portion coupled by a spring, in which the second portion is connected to a third vertex of the triangular member and the first portion is connected to a second stage by a second pin in which the first portion pivots about the second pin, and
the triangular member is rotated about a pivot axis line of said lever when said lever is rotated, and the second stage is moved along the slide guide by a cam mechanism between the triangular member and the first and second rods.

5. A capillary electrophoresis apparatus comprising:
a capillary array having a capillary with which a migration medium can be filled, a capillary head which is provided at one end of the capillary, a load header which is provided at the other end of the capillary, an array sheet which supports the capillary, and an optical detection unit which optically detects a sample electrically migrated in the capillary;
a thermostatic device which accommodates the capillary array to keep the capillary at a constant temperature; and
a migration medium filling mechanism which fills the capillary with a migration medium,
wherein:
the end of the array sheet has two projections,
the front ends of the projections have pawls respectively so as to face each other,
the capillary head has a cylindrical front end, a conical portion, a cylindrical portion, and a disk-shaped collar portion,
the collar portion having notches at both ends in a diameter direction, the notches are configured to engage the two projections at end portions of the array sheet respectively, and
the capillary is provided along the surface of the array sheet.

6. The capillary electrophoresis apparatus according to claim 5,
wherein a first gap is provided between the collar portion and the array sheet in an axis line direction and a second gap is provided between the collar portion and the array sheet in a radial direction when the notches of collar portion are engaged with the projections at the end portion of the array sheet.

7. The capillary electrophoresis apparatus according to claim 5,
wherein the collar portion is engaged with a groove in the thermostatic device such that the capillary head can be moved in predetermined ranges in the axis line direction and the radial direction.

8. A capillary electrophoresis apparatus comprising:
a capillary array having a capillary with which a migration medium can be filled and a capillary head which is provided at one end of the capillary;
an optical detection unit which optically detects a sample electrically migrated in the capillary; and
a migration medium filling mechanism which fills the capillary with a migration medium,
wherein:
the capillary head is held at a predetermined position and the migration medium filling mechanism has a block having a first portion to which a syringe is attached and a second portion including a hole in which the capillary head is engaged,
the syringe fills the capillary with the migration medium through the hole, and a slide mechanism which moves the block along a path parallel to a central axis line of the capillary head such that the central axis line of the capillary head is aligned with a central axis line of the hole,
the slide mechanism has two slide guides which are arranged in parallel to each other, first and second stages which are movable along the slide guide, a spring which connects the first and second stares, a block support member which connects the first stage to the block, and a drive mechanism which drives the second stage along the slide guide,
a flow path of the first portion and the hole of the second portion are connected by a tube, and
the first stage and the second portion are connected by the block support member.

9. A capillary electrophoresis apparatus comprising:
a capillary comprising a negative electrode end, wherein said capillary is configured to be filled with a migration medium;
an optical detection unit configured to optically detect a sample that electrically migrates in the capillary;
a high-voltage power supply configured to apply a high voltage across said capillary;
a vessel comprising:
a lower-side sample storage unit configured to hold a sample;
an upper-side buffer storage unit configured to hold a buffer,
said sample and said buffer being separated from each other by an air layer,
said lower-side sample storage unit having a cross section smaller than that of said upper-side buffer storage unit;
a shoulder formed at a boundary between said lower-side sample storage unit and said upper-side buffer storage unit; and
a conveyance device configured to convey the vessel to said negative-electrode end and to vertically move said capillary vessel.

10. A capillary electrophoresis apparatus comprising:
a capillary comprising a negative-electrode end, wherein said capillary is configured to be filled with a migration medium;
an optical detection unit configured to optically detect a sample that electrically migrates in said capillary;
a high-voltage power supply configured to apply a high voltage across said capillary;
a vessel comprising:
a lower-side sample storage unit comprising an inner wall and configured to hold a sample,
an upper-side buffer storage unit configured to hold a buffer,
said lower side sample storage unit formed by a recess made in the bottom surface of said upper-side buffer storage unit,
a partition wall configured to divide said vessel into two portions,
said partition wall extending from an opening of said vessel to near the bottom surface of said lower-side sample storage unit forming a first gap between said bottom surface of said lower-side sample storage unit,
said partition wall further forming a second gap between said inner wall of said lower-side sample storage unit,
said sample and said buffer being separated from each other by an air layer formed in said second gap between said partition wall and said inner wall of said lower-side sample storage unit; and
a conveyance device configured to convey the vessel to said negative-electrode end and to vertically move said vessel.

11. A capillary electrophoresis apparatus comprising:
a capillary comprising a negative-electrode end, wherein said capillary is configured to be filled with a migration medium;
an optical detection unit configured to optically detect a sample that is electrically migrated in said capillary;
a high-voltage power supply configured to apply a high voltage across said capillary; and
a vessel comprising:
a lower-side buffer storage unit configured to hold a buffer,
an upper-side sample storage unit configured to hold a sample, and
said lower-side buffer storage unit and said upper-side sample storage unit having a stacked structure and said upper-side sample storage unit having a bottom formed of a first film.

12. The capillary electrophoresis apparatus according to claim 11, further comprising a second film which is obliquely provided below the first film, and the second film being obliquely stretched with respect to a horizontal plane.

13. The capillary electrophoresis apparatus according to claim 12, further comprising a distilled water storage unit comprising a bottom unit formed of a third film, said distilled water storage unit provided above said upper-side sample storage unit and configured to store distilled water.

14. A capillary electrophoresis apparatus comprising:
a capillary array having a capillary with which a migration medium can be filled, an array sheet which supports the capillary, and an optical detection unit which optically detects a sample electrically migrated in the capillary; and
a thermostatic device which accommodates the capillary array to keep the capillary at a constant temperature,
wherein the thermostatic device has a main body frame and a door frame which is engaged with the main body frame, a temperature control member having a temperature control function is provided in the main body frame, and the capillary is in contact with the temperature control member in the thermostatic device, wherein:
a hole is provided in the temperature control member. an optical detection unit holder is arranged in the hole to hold the optical detection unit, an optical detection unit holder cover is provided in the optical detection unit holder to press the optical detection unit held by the optical detection unit holder, and
a single temperature control device is provided as the temperature control member, which controls not only the temperature of the capillary but also the temperatures of the optical detection unit, the optical detection unit holder, and the optical detection unit holder cover when the optical detection unit holder holds the optical detection unit.

15. The capillary electrophoresis apparatus according to claim 14, wherein the optical detection unit holder cover has a temperature propagation member, and the temperature propagation member contacts the temperature control member.

16. The capillary electrophoresis apparatus according to claim 15, wherein the optical detection unit holder is made of a material having a coefficient of thermal conductivity smaller than that of the temperature propagation member of the optical detection unit holder cover.

17. The capillary electrophoresis apparatus according to claim 15, further comprising an optical system frame, which holds a lens or an optical filter which is in contact with the optical detection unit holder is made of a material having a coefficient of thermal conductivity smaller than that of the optical detection unit holder.

* * * * *